US011369798B2

(12) United States Patent
Cao et al.

(10) Patent No.: US 11,369,798 B2
(45) Date of Patent: *Jun. 28, 2022

(54) ATRIAL SYNCHRONIZED VENTRICULAR PACING SYSTEM USING INTRACARDIAC PACEMAKER AND EXTRACARDIAC ATRIAL SENSING

(71) Applicant: Medtronic, Inc., Minneapolis, MN (US)

(72) Inventors: Jian Cao, Shoreview, MN (US); Paul J. Degroot, Shoreview, MN (US); Todd J. Sheldon, North Oaks, MN (US)

(73) Assignee: Medtronic, Inc., Minneapolis, MN (US)

( * ) Notice: Subject to any disclaimer, the term of this patent is extended or adjusted under 35 U.S.C. 154(b) by 339 days.

This patent is subject to a terminal disclaimer.

(21) Appl. No.: 16/509,924

(22) Filed: Jul. 12, 2019

(65) Prior Publication Data

US 2019/0329045 A1    Oct. 31, 2019

Related U.S. Application Data

(63) Continuation of application No. 14/950,952, filed on Nov. 24, 2015, now Pat. No. 10,350,417.

(Continued)

(51) Int. Cl.
*A61N 1/365* (2006.01)
*A61N 1/37* (2006.01)
(Continued)

(52) U.S. Cl.
CPC .......... *A61N 1/36514* (2013.01); *A61B 5/349* (2021.01); *A61B 5/352* (2021.01); *A61B 5/686* (2013.01); *A61B 5/7292* (2013.01); *A61N 1/36585* (2013.01); *A61N 1/3702* (2013.01); *A61N 1/3756* (2013.01); *A61N 1/37288* (2013.01)

(58) Field of Classification Search
CPC ............ A61N 1/36514; A61N 1/36585; A61N 1/3702; A61N 1/37288; A61N 1/3756; A61B 5/349; A61B 5/352; A61B 5/353; A61B 5/36; A61B 5/686; A61B 5/7292
See application file for complete search history.

(56) References Cited

U.S. PATENT DOCUMENTS 4,987,897 A    1/1991 Funke
5,113,859 A    5/1992 Funke
(Continued)

OTHER PUBLICATIONS

C00001535.WOU3 (PCT/US2015/062645) PCT Notification of Transmittal of the International Search Report and the Written Opinion of the International Searching Authority, dated Feb. 15, 2016, 11 pages.

*Primary Examiner* — Tammie K Marlen

(57) ABSTRACT

An implantable medical device system includes an extracardiac sensing device and an intracardiac pacemaker. The sensing device senses a P-wave attendant to an atrial depolarization of the heart via housing-based electrodes carried by the sensing device when the sensing device is implanted outside the cardiovascular system and sends a trigger signal to the intracardiac pacemaker in response to sensing the P-wave. The intracardiac pacemaker detects the trigger signal and schedules a ventricular pacing pulse in response to the detected trigger signal.

19 Claims, 13 Drawing Sheets

Related U.S. Application Data

(60) Provisional application No. 62/084,639, filed on Nov. 26, 2014.

(51) Int. Cl.
*A61N 1/372* (2006.01)
*A61B 5/00* (2006.01)
*A61N 1/375* (2006.01)
*A61B 5/349* (2021.01)
*A61B 5/352* (2021.01)

(56) References Cited

U.S. PATENT DOCUMENTS

| | | |
|---|---|---|
| 6,445,953 B1 | 9/2002 | Bulkes et al. |
| 7,428,438 B2 | 9/2008 | Parramon et al. |
| 7,925,343 B1 | 4/2011 | Min et al. |
| 7,991,467 B2 | 8/2011 | Markowitz et al. |
| 8,532,875 B2 | 9/2013 | Engelhardt et al. |
| 8,744,572 B1 | 6/2014 | Greenhut et al. |
| 9,168,380 B1 | 10/2015 | Greenhut et al. |
| 9,492,671 B2 | 11/2016 | Richard |
| 9,669,224 B2 | 6/2017 | Carney et al. |
| 9,999,774 B2 | 6/2018 | Cinbis et al. |
| 2004/0059392 A1 | 3/2004 | Parramon et al. |
| 2004/0106954 A1 | 6/2004 | Whitehurst et al. |
| 2006/0085039 A1 | 4/2006 | Hastings et al. |
| 2006/0135999 A1 | 6/2006 | Bodner et al. |
| 2008/0294210 A1 | 11/2008 | Rosero |
| 2011/0071586 A1 | 3/2011 | Jacobson |
| 2013/0282073 A1 | 10/2013 | Cowan et al. |
| 2014/0121719 A1 | 5/2014 | Bonner et al. |
| 2014/0330326 A1 | 11/2014 | Thompson-Nauman et al. |

ATRIAL SYNCHRONIZED VENTRICULAR PACING SYSTEM USING INTRACARDIAC PACEMAKER AND EXTRACARDIAC ATRIAL SENSING

REFERENCE TO RELATED APPLICATIONS

This application is a continuation of U.S. application Ser. No. 14/950,952 filed Nov. 24, 2015, issued as U.S. Pat. No. 10,350,417 on Jul. 16, 2019, which claims the benefit of U.S. Provisional Application No. 62/084,639, filed on Nov. 26, 2014, the entire contents of which are incorporated by reference herein.

TECHNICAL FIELD

The disclosure relates to an implantable medical device system and associated method for sensing cardiac electrical signals using an extracardiac sensing device and delivering therapeutic stimulation pulses using a triggered intracardiac pacemaker.

BACKGROUND

Implantable pacemakers and cardioverter defibrillators (ICDs) are available for delivering electrical stimulation therapies to a patient's heart, such as bradycardia pacing, cardiac resynchronization therapy (CRT), anti-tachycardia pacing (ATP) and cardioversion/defibrillation shocks. Pacemakers and ICDs generally sense cardiac electrical signals via electrodes coupled to the pacemaker or ICD. The cardiac electrical signals, such as an electrocardiogram (ECG) or intracardiac electrogram (EGM), are used to determine a need for electrical stimulation therapies and control the proper timing of pacing pulses based on sensed cardiac electrical signals.

Some pacemakers are implanted in a subcutaneous pocket and are coupled to transvenous leads carrying endocardial electrodes that are advanced within the heart. Advancement of medical device technology has led toward smaller and smaller implantable devices. Recently, intracardiac pacemakers have been introduced, which can be implanted directly in a heart chamber. An intracardiac pacemaker may carry electrodes directly on the housing of the pacemaker and eliminate the need for transvenous leads, which can have several advantages. For example, complications due to infection associated with a lead extending from a subcutaneous pacemaker pocket transvenously into the heart can be eliminated. Other complications, such as "Twiddler's syndrome," are eliminated with the use of an intracardiac pacemaker.

SUMMARY

In general, the disclosure is directed to techniques for delivering atrial-synchronized ventricular pacing by an IMD system including an extracardiac sensing device and an intracardiac pacemaker. The extracardiac sensing device may be implanted outside the cardiovascular system, e.g., subcutaneously, submuscularly or intra-thoracically, and includes housing electrodes for sensing cardiac electrical signals. The sensing device transmits trigger signals to the intra-cardiac pacemaker to cause the pacemaker to deliver a ventricular pacing pulse synchronized to a P-wave sensed by the sensing device.

In one example, the disclosure provides a method for providing pacing stimuli to a heart of a patient comprising sensing a P-wave by an extracardiac sensing device via housing-based electrodes when the sensing device is implanted in a patient and outside the patient's cardiovascular system, generating a trigger signal by the sensing device in response to sensing the P-wave, detecting the trigger signal by an intracardiac pacemaker; and scheduling a ventricular pacing pulse by the intracardiac pacemaker in response to the detected trigger signal.

In another example, the disclosure provides an implantable medical device system including an extracardiac sensing device and an intracardiac pacemaker. The extracardiac sensing device includes a housing; a plurality of housing-based electrodes; a sensing module enclosed by the housing and configured to sense a P-wave attendant to an atrial activation of a patient's heart via the housing-based electrodes when the sensing device is implanted in a patient outside the cardiovascular system; a trigger signal generator; and a control module configured to control the trigger signal generator to transmit a trigger signal in response to the sensing module sensing the P-wave. The intracardiac pacemaker includes a trigger signal detector, a pacing pulse generator; and a control module configured to schedule a pacing pulse in response to the trigger signal detector detecting the trigger signal.

In another example, the disclosure provides an extracardiac sensing device comprising a housing; a plurality of housing-based electrodes; a sensing module configured to sense cardiac electrical events via the housing-based electrodes when the sensing device is implanted in a patient outside the patient's cardiovascular system; a trigger signal generator configured to transmit a wireless trigger signal to an intracardiac pacemaker to cause the pacemaker to deliver a cardiac pacing pulse, a signal detector configured to detect a wireless event signal transmitted to the sensing device by the intracardiac pacemaker, and a control module coupled to the sensing module, the trigger signal generator and the signal detector and configured to control the trigger signal generator to generate the wireless trigger signal in response to the sensing module sensing a cardiac electrical event, set a blanking interval to inhibit sensing a next cardiac electrical event during the blanking interval in response to the signal detector detecting the wireless event signal transmitted by the intracardiac pacemaker.

In yet another example, the disclosure provides a non-transitory computer readable storage medium storing instructions which, when executed by a control module of an extracardiac sensing device and a control module of an intracardiac pacemaker of an implantable medical device system, cause the system to sense a P-wave attendant to an atrial depolarization of the heart by the sensing device via housing-based electrodes carried by the sensing device, send a trigger signal from the sensing device to the intracardiac pacemaker, detect the trigger signal by the pacemaker, and schedule a ventricular pacing pulse by the intracardiac pacemaker in response to the detected trigger signal.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

DETAILED DESCRIPTION

An implantable medical device (IMD) system and associated techniques are disclosed herein for sensing electrocardiogram (ECG) signals by a sensing device using electrodes implanted outside the cardiovascular system (such as outside the heart at a subcutaneous, sub-muscular or intrathoracic location) and triggering an intracardiac pacemaker to deliver atrial-synchronized ventricular pacing pulses in response to the sensed ECG signals. The sensing device may be leadless and is typically implanted subcutaneously, although alternative implant locations may be sub-muscular or intrathoracic locations. The sensing device is configured to sense extracardiac ECG signals for triggering the intracardiac pacemaker to deliver an automatic therapy to the patient's heart based on the timing of the sensed ECG signals. A trigger signal is initiated by the sensing device and detected by a transducer included in the pacemaker. Automatic therapy delivery is achieved by the separate sensing and therapy delivery devices, without requiring the two devices to be physically connected to each other.

Among other things, elimination of the physical connection between the sensing and therapy delivery components of an IMD system enables minimally invasive implant procedures to be used, down-sizing of IMD system components and power supply, and/or elimination of some components, such as medical leads, sensing capability in the intracardiac pacemaker, and a radio frequency (RF) transmitter in the intracardiac pacemaker. The sensing device of the IMD system described herein is implanted outside the cardiovascular system, typically subcutaneously, thus making it easier to implant than a device implanted in the cardiovascular system it does not include any leads, which may increase its usable life and reduce complications as compared to a sensing device with one or more leads.

As used herein, a "trigger signal" is a signal emitted by a transducer when an electrical signal is applied to the transducer. The trigger signal is a command, which is generated by and sent from the sensing device to the intracardiac pacemaker to trigger the delivery of therapy by the pacemaker upon detection of the trigger signal. Examples of a trigger signal include an acoustical signal, e.g. sound waves having a frequency in the ultrasonic range produced by an acoustical transducer, an optical signal produced by a light emitting diode (LED), vertical cavity surface emitting laser (VCSEL) or other optical transducer, an RF signal emitted by an RF antenna or a signal transmitted by tissue conductance communication (TCC).

Figure 1:
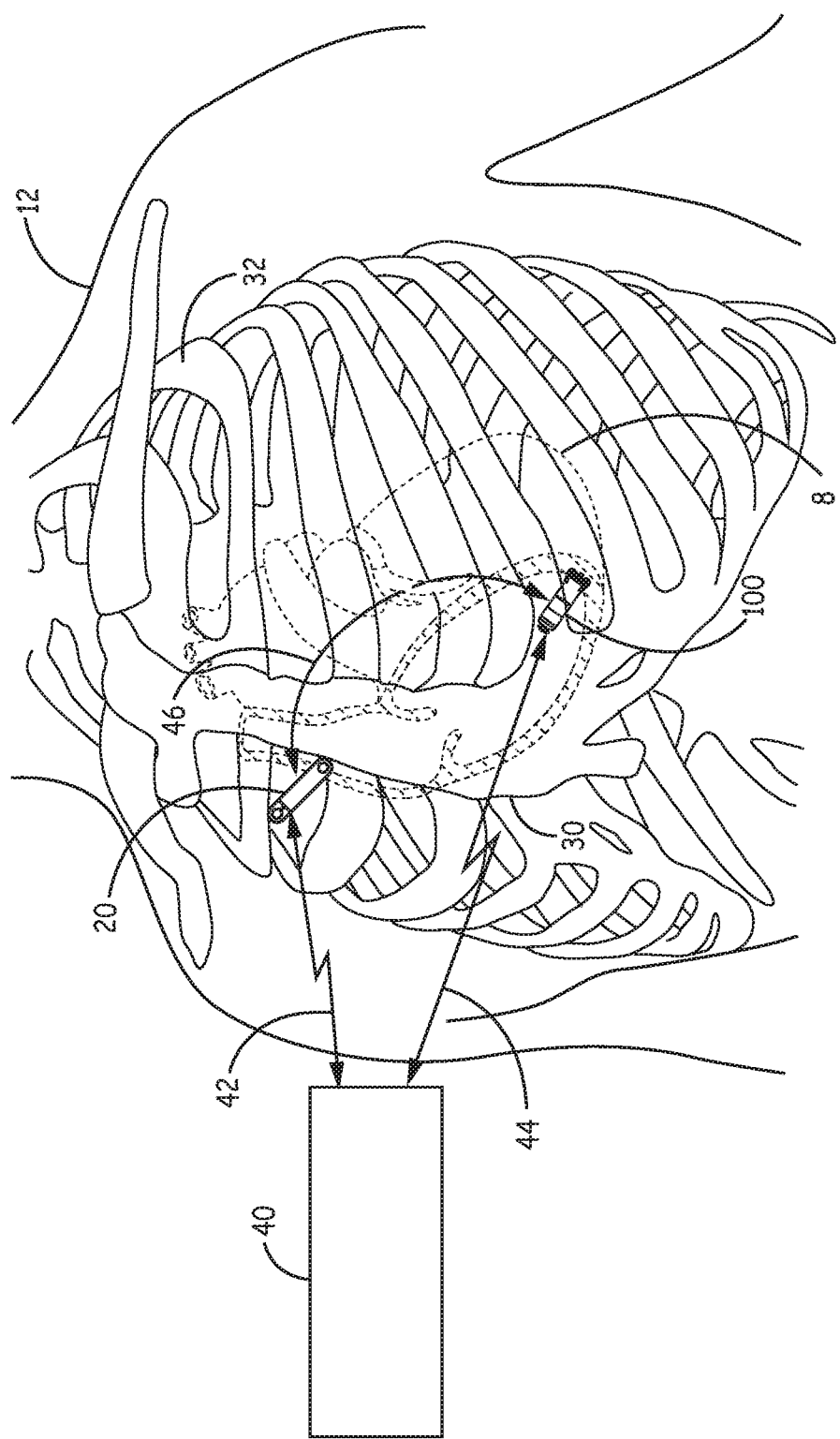
FIG. 1 is a conceptual drawing, illustrating an IMD system capable of sensing cardiac electrical signals in a patient and providing therapy to the heart the of patient.

FIG. 1 is a conceptual drawing, illustrating an IMD system 10 capable of sensing cardiac electrical signals in a patient and providing therapy to the heart 8 of patient 12. IMD system 10 includes a therapy delivery device embodied as an intracardiac pacemaker 100 and a leadless, subcutaneous sensing device 20. Sensing device 20 is provided as leadless, miniaturized device that can be implanted subcutaneously for sensing atrial P-waves. In some examples, sensing device 20 is an injectable device. Sensing device 20 acquires cardiac electrical signals using housing based electrodes and is configured to reliably sense atrial P-waves.

Intracardiac pacemaker 100 is shown implanted within the right ventricle (RV) of heart 8, for example along the ventricular apex. Intracardiac pacemaker 100 may sense a ventricular EGM signal using electrodes located along the housing of pacemaker 100. The low amplitude of atrial P-waves in a ventricular EGM signal makes sensing of P-waves by pacemaker 100 challenging. By including sensing device 20, IMD system 10 is capable of providing reliable dual chamber (atrial and ventricular) sensing.

Sensing device 20 may be implanted superior to the fourth intercostal space to obtain an ECG signal with increased atrial P-wave signal strength relative to the P-wave signal strength that might be received at other implant locations, e.g., at or below the fourth intercostal space. Sensing device 20 senses P-waves and optionally R-waves from the acquired ECG signal. In response to sensing a P-wave, sensing device 20 transmits a trigger signal to pacemaker 100. In response to receiving a trigger signal, pacemaker 100 schedules a ventricular pacing pulse. In the absence of a sensed intrinsic R-wave prior to the scheduled ventricular pacing pulse, pacemaker 100 delivers the ventricular pacing pulse synchronized to the sensed P-wave without requiring P-wave sensing by pacemaker 100. The ventricular pacing pulses are delivered using the housing-based electrodes of the intracardiac pacemaker 100.

Sensing device 20 is shown implanted along the second intercostal space to the right of sternum 30. In other examples, sensing device 20 may be implanted to the left or the right of sternum 30, over sternum 30 or under sternum 30. Sensing device 20 is generally implanted extrathoracically, outside of ribcage 32, subcutaneously or submuscularly, but in other examples, sensing device 20 may be implanted beneath ribcage 32 or sternum 30. Other possible implant locations of sensing device 20 are described below in conjunction with FIG. 2.

Pacemaker 100 is a transcatheter intracardiac pacemaker adapted for implantation wholly within the heart 8 and may be wholly implantable within a single heart chamber, e.g., wholly within the RV or wholly within the LV. In the example of FIG. 1, pacemaker 100 is positioned proximate to an inner wall of the RV to provide right ventricular pacing. In other examples, pacemaker 100 may be positioned at other locations outside or within heart 8, including epicardial locations. For example, pacemaker 100 may be positioned outside or within the right ventricle to provide right ventricular pacing triggered by signals received from sensing device 20.

Pacemaker 100 is capable of producing electrical stimulation pulses delivered to the heart 8 via one or more electrodes on the outer housing of pacemaker 100. Pacemaker 100 is a triggered pacemaker and therefore includes a receiving transducer for receiving a trigger signal emitted by sensing device 20. In response to detecting the trigger signal, pacemaker 100 delivers one or more pacing pulses. A "triggered pacemaker" as used herein is a device that is triggered to deliver a therapy to the patient's heart (or another targeted patient tissue such as a vagal nerve) by a trigger signal transmitted by another implanted device. In the illustrative embodiments described herein, the intracardiac pacemaker 100 delivers an electrical stimulation therapy, such as atrial-synchronized ventricular pacing pulses.

The triggered pacemaker 100 includes a transducer that produces an electrical signal in response to being subjected to the trigger signal. The transducer may be an antenna for receiving an RF trigger signal, electrodes and a receiver for receiving a TCC signal, or other type of transducer such as an acoustical transducer or an optical transducer as generally disclosed in commonly-assigned U.S. patent application Ser. No. 14/695,013, U.S. patent application Ser. No. 14/694,990 and to U.S. patent application Ser. No. 14/695,004, all filed on Apr. 23, 2015 and incorporated herein by reference in their entirety. Communication between triggered pacemaker 100 and sensing device 20 may be by a TCC system incorporating aspects generally disclosed in U.S. Pat. No. 4,987,897 (Funke), incorporated herein by reference in its entirety. An acoustic body bus communication system may be implemented in IMD system 10 in other examples. An acoustic body bus communication system is generally disclosed in U.S. Pat. No. 5,113,859, (Funke), incorporated herein by reference in its entirety.

The electrical signal produced by the receiving transducer may be compared to a trigger signal detection threshold. When the trigger signal detection threshold is exceeded, pacemaker 100 may deliver a therapeutic stimulation pulse to a targeted tissue of the patient. The "triggered pacemaker" as disclosed herein, therefore, is, at least some of the time, not making a decision to schedule a pacing pulse therapy based on sensing and processing of a physiological signal sensed by the pacemaker 100 itself, such as a sensed cardiac electrical signals, sensed blood pressure signal, or other physiological signal acquired using a sensor or transducer that produces a time-varying signal waveform (e.g. ECG, blood pressure, etc.) correlated to a physiological condition or physiological events. The decision to schedule a pacing pulse is made by sensing device 20, which is controlling the transmission of a trigger signal to pacemaker 100 to cause pacemaker 100 to schedule one or more pacing pulses.

Pacemaker 100 may, however, sense a signal that causes a pacing pulse scheduled in response to a trigger signal to be inhibited or canceled. For example, if pacemaker 100 is configured to sense R-waves from a ventricular EGM signal, a pacing pulse scheduled in response to receiving a trigger signal from sensing device 20 may be canceled in response to sensing an R-wave after receiving the trigger signal and prior to delivering the pacing pulse.

While FIG. 1 shows one pacemaker 100 positioned in one heart chamber (the RV), it is contemplated that a second, triggered intracardiac pacemaker is positioned in the left ventricle (LV) in some examples. Both the RV pacemaker 100 and the second LV intracardiac pacemaker may receive a trigger signal emitted by sensing device 20 to coordinate biventricular pacing in response to P-waves sensed by sensing device 20 according to the techniques disclosed herein.

Pacemaker 100 includes a pulse generator configured to deliver one or more pacing pulses upon receiving the trigger signal from sensing device 20. Pacemaker 100 may not be configured to sense cardiac signals. Cardiac signal sensing is performed by sensing device 20. Sensing device 20 senses ECG signals and controls pacing delivered by pacemaker 100 via trigger signals under the control of sensing device 20.

In other examples, pacemaker 100 senses cardiac EGM signals in the heart chamber in which it is implanted. Since pacemaker 100 may be positioned wholly within a heart chamber, e.g., the RV, the EGM signal sensed by pacemaker 100 will be less sensitive or insensitive to P-waves and/or R-waves occurring in other heart chambers. In the example shown, pacemaker 100 may sense ventricular R-waves from an EGM signal received by housing-based electrodes, but P-wave sensing may be limited or non-existent due to the small P-wave signal amplitude present in the ventricular EGM signal.

Since pacemaker 100 may have no or limited sensing capabilities, pacemaker 100 may be "blinded" to events occurring in other heart chambers, such as the atria. Delivery of CRT, atrial-synchronized ventricular pacing, or other pacing therapies may require delivering a pacing pulse at a predetermined time interval after an event, sensed or paced, in another heart chamber. As such, sensing device 20 provides a trigger signal to pacemaker 100 in response to P-waves sensed from ECG signals acquired by sensing device 20 to cause pacing pulses to be delivered by pacemaker 100 at desired time intervals relative to atrial P-waves. Pacemaker 100 (for generating ventricular pacing pulses) combined with sensing device 20 (for sensing atrial P-waves and optionally R-waves and making pacing therapy delivery decisions in response thereto) provides the functionality required to deliver atrial-synchronized ventricular pacing without physical connection between pacemaker 100 and sensing device 20 implanted at separate sites. Sensing device 20 may be implanted at a location that optimizes P-wave sensing reliability as described below in conjunction with FIG. 2.

The system 10 illustrated in FIG. 1 is an example configuration of an IMD system and should not be considered limiting of the techniques described herein. Other arrangements of a sensing device coupled to sensing electrodes for sensing ECG signals and transmitting trigger signals to a triggered pacemaker for detecting the trigger signal and delivering a pacing pulse in response thereto may be conceived. Such systems may implement the techniques disclosed herein for identifying P-waves for use in controlling a trigger signal generator incorporated in sensing device 20 or separate from sensing device 20 to cause the pacemaker 100 to deliver therapy without requiring physical connection between the pacemaker 100 and the sensing device 20.

An external device 40 is shown in telemetric communication with sensing device 20 and pacemaker 100 by respective communication links 42 and 44. External device 40 may include a processor, display, user interface, telemetry unit and other components for transmitting and receiving data via communication links 42 and 44 and for displaying data to a user and receiving user input. Communication links 42 and 44 may be established using a radio frequency (RF) link such as BLUETOOTH®, Wi-Fi, or Medical Implant Communication Service (MICS) or other RF or communication frequency bandwidth.

External device 40 may be embodied as a programmer used in a hospital, clinic or physician's office to retrieve data from sensing device 20 and pacemaker 100 and to program operating parameters and algorithms in sensing device 20 and pacemaker 100 for controlling sensing and therapy delivery functions. External device 40 may be used to program sensing control parameters used by sensing device 20 and therapy control parameters used by pacemaker 100. Data stored or acquired by sensing device 20 and pacemaker 100, including physiological signals or associated data derived therefrom, results of device diagnostics, and histories of detected rhythm episodes and delivered therapies, may be retrieved from sensing device 20 and/or pacemaker 100 following an interrogation command. External device 40 may alternatively be embodied as a home monitor or hand held device.

Figure 2:
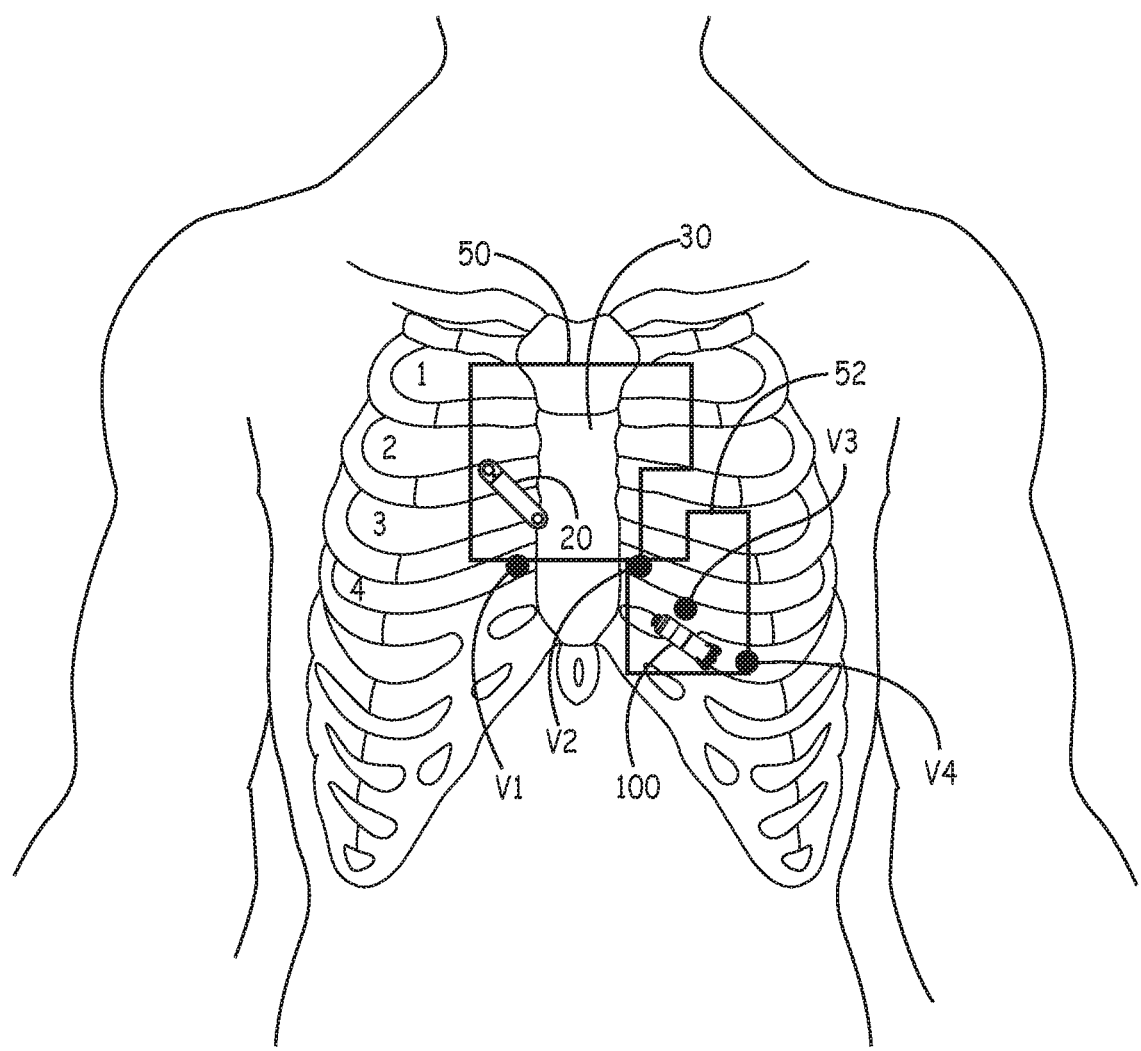
FIG. 2 is a conceptual drawing illustrating a targeted implant region for possible implant locations, substernal or subcutaneous, of the sensing device of FIG. 1.

FIG. 2 is a conceptual drawing illustrating a targeted implant region for possible implant locations, substernal, submuscular or subcutaneous, of sensing device 20. Sensing device 20 is implanted at a location that results in maximized P-wave amplitude for promoting reliable sensing of P-waves. The approximate target implant area indicated by boundary 50 is at or above the fourth intercostal space including regions to the right and left of the sternum 30. Within the target implant region indicated by boundary 50, the R-wave of an acquired ECG signal is not maximized. The implant location of sensing device 20 may be selected to have a high signal strength of P-waves relative R-waves in the acquired ECG signal.

The standard placement of V1 through V3 chest electrodes for surface ECG leads is shown. The V1 and V2 electrodes are at the fourth intercostal space. V1 is to the right of sternum 30, and V2 is to the left of sternum 30. V4 is placed at the 5th intercostal space at the left midclavicular line. V3 is positioned at a midpoint directly between V2 and V4. V5 is placed at fifth intercostal space on the anterior axillary line. V6 is placed at the fifth intercostal space at the left midaxillary line. Sensing device 20 is implanted in a targeted implant region that extends superiorly from the V1 and V2 level and approximately one to three inches to the left or the right of sternum 30. At approximately the first and second intercostal spaces, the targeted implant region may extend further to the left of sternum 30 than at the third and fourth intercostal spaces as indicated by boundary 50. Sensing device 20 may be implanted up to four inches superior to the further intercostal space. In other examples, sensing device 20 is implanted between two and three inches above the fourth intercostal space, to the right of sternum 30 and adjacent to sternum 30.

Boundary 52 indicates an approximate region of maximized R-wave amplitude in the ECG signal acquired by sensing device 20. This region indicated by boundary 52 marks a region that implantation of sensing device 20 is avoided in some examples to avoid an ECG signal with a prevalent R-wave and minimized P-wave. Intracardiac pacemaker 52 is positioned within the approximate boundary 52 when implanted in the RV.

The right border of heart 8 (not shown in FIG. 2) corresponding to the right atrium is approximately 1 cm to the right of the 3rd costal cartilage. The left border of the heart 8 corresponding to the left atrium is approximately 2 cm to the left of the 2nd costal cartilage. These borders may be used in identifying an appropriate implant site for sensing device 20. In general moving sensing device 20 further superior and/or further to the right of the V2 location promotes higher P-wave amplitude and lower R-wave amplitude in the acquired ECG signal. While the R-wave amplitude is lower in the region indicated by boundary 50, the R-wave may still be readily sensed in the acquired ECG signal since the R-wave amplitude may be on the order of approximately 1 mV or more. In comparison, even when P-wave signal strength is maximized by implanting sensing device 20 in the region marked by boundary 50, P-wave signal amplitude may be on the order of 0.1 mV or less. As described below, sensing of R-waves by sensing device 20 or by pacemaker 100 may be used to identify a P-wave sensing window for improving P-wave sensing reliability.

Sensing device 20 is shown at an approximately 45 degree angle relative to a vertical or lateral plane of patient 12. Optimal P-wave (and R-wave) sensing may be obtained when sensing device 20 is implanted at an approximate 45 degree angle within the region marked by boundary 50.

Figure 3A:
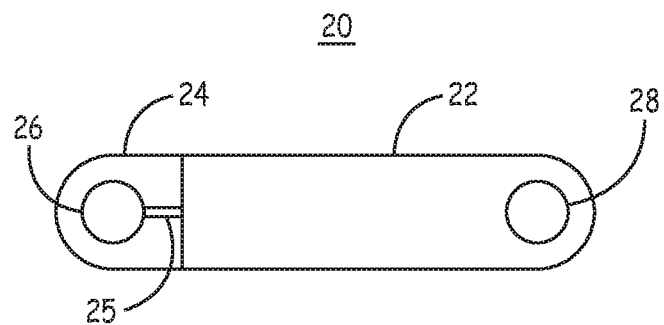
FIG. 3A is a conceptual diagram of the sensing device of FIG. 1.

FIG. 3A is a conceptual diagram of sensing device 20. Sensing device 20 includes a housing 22 that forms a hermetic seal that protects components within sensing device 20. Housing 22 may be formed of a conductive material, such as stainless steel or titanium alloy or other biocompatible conductive material or a combination of conductive and non-conductive materials. The housing 22 encloses one or more components, including one or processors, memory, a transceiver, sensing circuitry, and other appropriate components (often referred to herein as modules).

A header 24 is coupled to housing 22 for carrying electrode 26 and insulating electrical connections between electrode 26 and a sensing module enclosed in housing 22. Electrode 26 is exposed on a surface of header 24. Header 24 encloses or encapsulates an electrical feedthrough 25 that extends from electrode 26 across housing 22 and electrically couples electrode 26 to the sensing module enclosed by housing 22. A second electrode 28 may be formed as an uninsulated portion of housing 22 and serves as a ground electrode. In some examples, the housing 14 may include an insulating coating. The entirety of the housing 22 may be insulated, but only electrode 28 uninsulated. Examples of insulating coatings include parylene, urethane, PEEK, or polyimide among others. In other examples, an insulating coating of housing 22 is not provided, and all of housing 22 may function as an electrode 28. Electrodes 26 and 28 may be, without limitation, titanium, platinum, iridium or alloys thereof. In FIG. 3A, housing 22 is generally rectangular with electrodes 26 and 28 positioned near opposing ends of housing 22. Electrodes 26 and 28 may be positioned approximately 2 to 5 cm apart in some examples for acquiring the ECG signal.

Figure 3B:
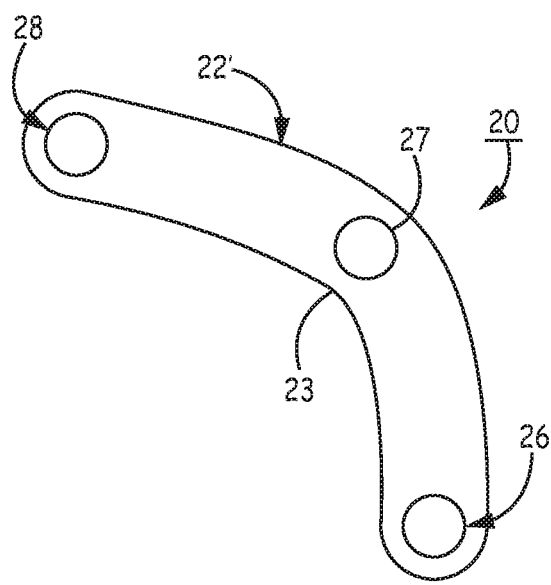
FIG. 3B is conceptual diagram of an alternative example of the sensing device of FIG. 1.

FIG. 3B is a conceptual diagram of an alternative example of sensing device 20. In this example, housing 22' may be non-linear, angular housing including a curve or bend 23. Housing 22' may carry three electrodes 26, 27 and 28 to provide multiple sensing vectors. Electrodes 26 and 28 may be carried at or near opposing ends of housing 22', and a third electrode 27 may be located between electrodes 26 and 28. Electrode 27 may be located at housing bend 23 such that one sensing vector between electrodes 28 and 27 is approximately horizontal and another sensing vector between electrode 26 and 27 is approximately vertical. Electrodes 26, 27 and 28 may be equally spaced, e.g., at 1 to 3 inches apart (with no limitation intended). The electrode spacing between electrodes 26, 27 and 28 may vary between embodiments. For example, without any limitation intended, electrodes 26 and 28 may be spaced apart approximately 1 inch to approximately 6 inches. In one example, the spacing between electrodes 26 and 28 is at least approximately 3 inches and no more than approximately 4 inches with electrode 27 positioned between electrodes 26 and 28. In other examples, electrodes 26, 27 and 28 may be unequally spaced from each other such that one vector between electrode 27 and one of electrodes 28 or 26 has a greater inter-electrode distance than the other vector between electrode 27 and the other of electrodes 26 and 28.

Electrodes 26 and 28 may be electrically isolated from housing 22' and electrically coupled to a circuitry enclosed by housing 22' via an electrical feedthrough crossing the wall of housing 22'. Electrode 27 may be electrically coupled to housing 22' and serve as a ground or return electrode coupled to sensing circuitry enclosed by housing 22'. Housing 22' may be an electrically conductive housing having an insulating coating with electrode 27 being an uninsulated, exposed portion of conductive housing 22'. The angular housing 22' and electrodes 26, 27 and 28 is one example of a sensing device 20 that includes multiple sensing vectors. Other housing and electrode arrangements are conceivable that would provide multiple sensing vectors.

Sensing device 20 of FIG. 3B may obtain cardiac electrical signals using a sensing vector between electrodes 26 and 27 and between electrodes 28 and 27. One vector may be selected for sensing R-waves from the ECG signal and the other vector may be selected for sensing P-waves from the ECG signal. In other examples, sensing device 20 may be configured to select a best vector for sensing cardiac signals and a best vector for communicating (e.g., transmitting or receiving a TCC signal to pacemaker 100). To illustrate, an ECG vector between electrodes 26 and 27 may be used to identify cardiac events for use in controlling trigger signals sent to pacemaker 100. For instance, P-waves may be sensed for controlling the TCC trigger signals sent to pacemaker 100 in timed relation to sensed P-waves to cause pacemaker 100 to schedule a ventricular pacing pulse at a desired AV interval. The TCC trigger signal may be transmitted using electrodes 28 and 27.

Figure 4A:
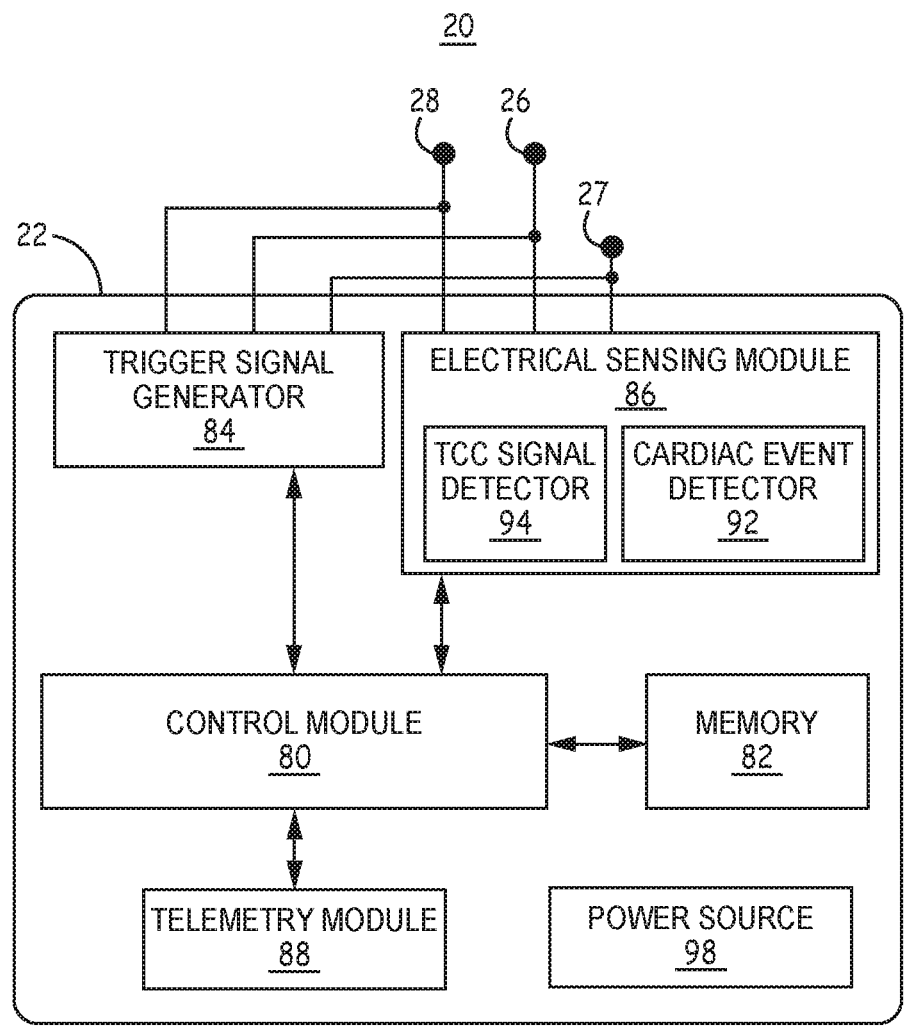
FIG. 4A is a functional block diagram of electronic circuitry that is included in one example of the sensing device shown in FIG. 1.

FIG. 4A is a functional block diagram of electronic circuitry that is included in one example of sensing device 20 shown in FIG. 1. Sensing device 20 includes a control module 80, memory 82, a trigger signal generator 84, electrical sensing module 86, telemetry module 88, and power source 98. Power source 98 provides power to the circuitry of sensing device 20, including each of the modules 80, 82, 84, 86, and 88 as needed. Power source 98 may include one or more energy storage devices, such as one or more rechargeable or non-rechargeable batteries.

The functional blocks shown in FIG. 4A represent functionality that may be included in sensing device 20 implemented as one or more discrete and/or integrated electronic circuit components that implement analog and/or digital circuits capable of producing the functions attributed to sensing device 20 herein. For example, the modules 80, 82, 84, 86 and 88 may include analog circuits, e.g., amplification circuits, filtering circuits, comparators, and/or other signal conditioning circuits. The modules 80, 82, 84, 86 and 88 may also include digital circuits, e.g., analog-to-digital converters, combinational or sequential logic circuits, integrated circuits, memory devices, state machines, etc.

Memory 82 may include any volatile, non-volatile, magnetic, or electrical non-transitory computer readable storage media, such as a random access memory (RAM), read-only memory (ROM), non-volatile RAM (NVRAM), electrically-erasable programmable ROM (EEPROM), flash memory, or any other memory device. Furthermore, memory 82 may include non-transitory computer readable media storing instructions that, when executed by one or more processing circuits, cause processor 80 or other sensing device modules to perform various functions attributed to sensing device 20. The non-transitory computer readable media storing the instructions may include any of the media listed above.

The functions attributed to the modules 80, 82, 84, 86, and 88 may be embodied as one or more processors, hardware, firmware, software, or any combination thereof. Depiction of different features as modules is intended to highlight different functional aspects and does not necessarily imply that such modules must be realized by separate hardware or software components. Rather, functionality associated with one or more modules may be performed by separate hardware, firmware or software components, or integrated within common hardware, firmware or software components. For example, cardiac rhythm detection operations for making a decision to trigger pacemaker 100 to deliver a pacing pulse may be implemented by a processor included in control module 80 that receives P-wave sensed event signals from electrical sensing module 86 and executes instructions stored in memory 82.

Electrical sensing module 86 is coupled to a sensing electrode vector in order to acquire a cardiac electrical signal including P-waves attendant to the depolarization of the atria and R-waves attendant to the depolarization of the ventricles. For example, electrical sensing module 86 may be coupled to a sensing electrode vector between housing-based electrodes 26 and 28 as shown in the example of FIG. 3A, where electrode 26 is electrically isolated from housing 22 and electrode 28 is a non-insulated portion of housing 22.

In another example, as shown in FIG. 3B, electrodes 26 and 28 may be both be electrically isolated from housing 22 and electrode 27 may serve as an additional electrode that may be selected with electrode 26 or electrode 28 for forming a sensing vector for sensing cardiac electrical signals. Electrical sensing module 86 may be enabled to selectively monitor one or more sensing vectors selected from the available electrodes 26, 27, and 28. For example, sensing module 86 may include switching circuitry for selecting which of electrodes 26, 27 and 28 are coupled to sense amplifiers or other signal detection circuitry included in sensing module 86. Switching circuitry may include a switch array, switch matrix, multiplexer, or any other type of switching device suitable to selectively couple sense amplifiers to selected electrodes.

Electrical sensing module 86 may include filters, amplifiers, analog-to-digital converter, a rectifier, comparator, and/or other circuitry for obtaining a filtered, amplified and rectified ECG signal. Electrical sensing module 86 includes a cardiac event detector 92 for sensing cardiac electrical signals (e.g., P-waves and R-waves) from the ECG signal. Cardiac event detector 92 may include a sense amplifier or other cardiac event detection circuitry for receiving the ECG signal developed across a sensing electrode vector and comparing the signal to a cardiac event sensing threshold, e.g., a P-wave sensing threshold or an R-wave sensing threshold. When more than one sensing electrode vector is available, the sensing vector having the highest P-wave amplitude (or lowest signal-to-noise ratio) may be selected.

The sensing module 86 may pass sensed event signals to control module 80 upon sensing a cardiac event. For example, sensed event signals are passed to control module 90 when the ECG signal crosses a P-wave sensing threshold, which may be an auto-adjusting sensing threshold. A higher R-wave sensing threshold may be set for sensing R-waves from the ECG signal, and an R-wave sensed event signal may be passed to control module 80.

In some examples, cardiac event detector 92 may include multiple sensing channels for sensing multiple ECG sensing vectors from available electrodes. For example, one sensing electrode vector may be coupled to one sensing channel for sensing P-waves and a different sensing electrode vector may be coupled to a second sensing channel for sensing R-waves. In other examples, two sensing channels may be used for sensing P-waves to improve reliability of P-wave sensing.

Sensing module 86 may also pass a digitized ECG signal to control module 80. Control module 80 may store ECG signal episodes in memory 82 for transmission to external device 40. Control module 80 may be configured to perform morphological analysis of digitized ECG signals for detecting and discriminating P-waves from R-waves, T-waves or noise signals.

In the example shown, sensing device 20 includes a trigger signal generator 84 coupled to electrodes 26, 27 and 28. In this example, trigger signal generator 84 may be configured to produce TCC signals transmitted via selected housing-based electrodes 26, 27 and/or 28. Upon receiving a P-wave signal, control module 80 may cause trigger signal generator 84 to transmit a TCC trigger signal via electrodes 26, 27 and/or 28 to pacemaker 100. TCC signal generator 84 may include an oscillator generating a carrier signal that is modulated to produce a desired TCC trigger signal, which may be 10 kHz to 100 kHz in frequency and amplified to an amplitude of 50 to 500 millivolts in some examples. TCC signal generator 84 may correspond to body bus transmitters generally disclosed in the above-incorporated '897 patent (Funke).

In other examples, sensing device 20 may not include the TCC trigger signal generator 84 and control module 80 may control telemetry module 88 to transmit a trigger signal as a RF communication signal to pacemaker 100. In this case, telemetry module 88 functions as a the trigger signal generator. Telemetry module 88 includes an antenna and RF transceiver for communication with external device 40 and in some cases for transmitting a trigger signal to pacemaker 100.

The trigger signal, emitted by TCC trigger signal generator 84 or by telemetry module 88, may be produced immediately, e.g., on the next clock signal, after receiving a P-wave sensed event signal for electrical sensing module 86. In other examples, the trigger signal may be transmitted after a pre-determined delay after receiving the P-wave sensed event signal, e.g., after a pre-determined AV delay or portion thereof.

In some examples sensing device 20 is configured to detect communication signals from pacemaker 100 indicating the occurrence of ventricular events, e.g., an R-wave sensed by pacemaker 100 or a pacing pulse delivered by pacemaker 100. As such, sensing device 20 may include a signal detector 94 shown in FIG. 4A as a TCC signal detector included in electrical sensing module 86 for detecting TCC signals produced by pacemaker 100. Pacemaker 100 may be configured to pass TCC signals to sensing device 20 when a pacing pulse has been delivered and/or when a cardiac electrical signal, e.g., an R-wave, has been sensed by pacemaker 100. In addition to sensing cardiac events from an acquired ECG signal by cardiac event detector 92, electrical sensing module 86 may be configured to detect ventricular event communication signals generated by pacemaker 100. For example, a TCC signal may be transmitted by pacemaker 100 to sensing device 20 to indicate that an R-wave has been sensed. Sensing device 20 may detect the TCC signal by TCC signal detector 94. TCC signal detector 94 may include a receiver having amplifiers, filters, demodulators, comparators and other circuitry for detecting a pre-defined pattern or characteristic of a TCC signal that is produced by pacemaker 100. TCC signal detector 94 may correspond to a body bus receiver as generally disclosed in the above-incorporated '897 patent (Funke).

In other examples, control module 80 may receive the digitized ECG signal from electrical sensing module 86 and analyze the signal for detecting communication signals received from pacemaker 100. The ventricular event communication signals produced by pacemaker 100 are communication signals intended to be received and detected by sensing device 20 as opposed to being therapeutic pacing pulses delivered to the heart by pacemaker 100.

Telemetry module 88 includes a transceiver and antenna for communicating with another device, such as an external programmer 40 and pacemaker 100 when pacemaker 100 is configured to receive wireless telemetry signals. Under the control of control module 80, telemetry module 88 may receive downlink telemetry from and send uplink telemetry to programmer 40 or other external device.

Telemetry module 88 may be controlled by control module 80 to transmit trigger signals in some examples. TCC trigger signal generator 84 may be optional in this case. For example, upon detecting a P-wave, sensing device 20 may control a transceiver included in telemetry module 88 to transmit an RF trigger signal to pacemaker 100 to cause pacemaker 100 to schedule one or more pacing pulses. As described above, sensing device 20 may include a TCC signal detector 94 configured to detect ventricular event signals from pacemaker 100. Additionally or alternatively, telemetry module 88 may be configured to receive ventricular event signals via the antenna and transceiver included in telemetry module 88. In this case, pacemaker 100 transmits ventricular event signals as wireless RF telemetry communication signals. Telemetry module 88 may receive and decode the ventricular event signals. Control module 80 receives notification of detected ventricular event signals from telemetry module 88. As such, a ventricular event signal detector included in sensing device 20 may include one or both of telemetry module 88 and TCC signal detector 94.

Figure 4B:
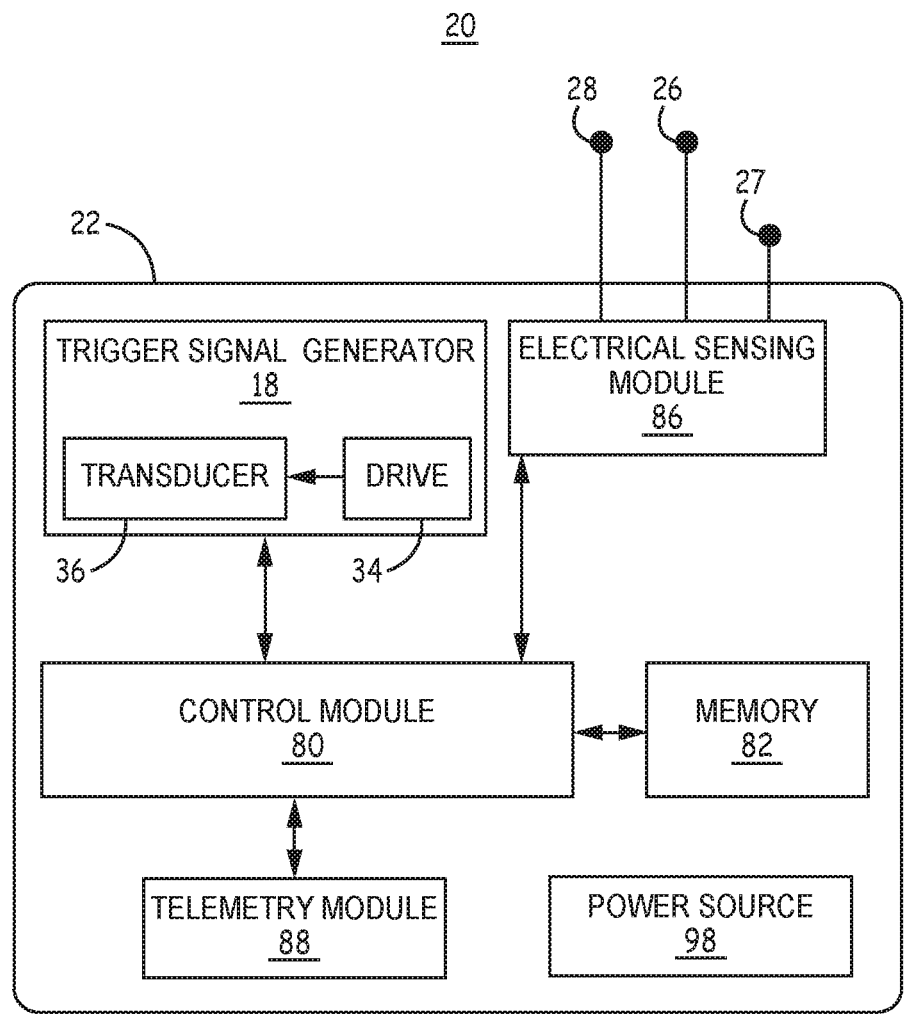
FIG. 4B is a functional block diagram of an alternative example of a sensing device.

FIG. 4B is a functional block diagram of an alternative example of sensing device 20. In this example, sensing device 20 includes a trigger signal generator 18 having a transducer 36 and a drive signal circuit 34 for producing a trigger signal in response to sensing a cardiac event, e.g., a P-wave, and triggering pacemaker 100 to schedule a pacing pulse. Trigger signal generator 18 may be an optical device or an acoustical device having an optical transducer or an acoustical transducer, respectively. Drive signal circuit 34 is controlled by control module 80 to pass an electrical drive signal or excitation signal to transducer 36 to cause transducer 36 to emit a trigger signal. When trigger signal generator 18 is implemented with an optical transducer, housing 22 may include an optically transparent window for passing light wavelengths included in the optical trigger signal. When trigger signal generator 18 is implemented with an acoustical transducer, housing 22 may include an acoustical coupling member for passing acoustical signals. Various examples of trigger signal emitting devices are generally disclosed in the above-incorporated U.S. patent application Ser. Nos. 14/695,013, 14/694,990, and 14/695,004.

Trigger signal generator 18 is shown enclosed within housing 22. In other examples, trigger signal generator 18 configured to produce acoustical or optical trigger signals may be a separate device that receives signals from sensing device 20, such as TCC communication signals or RF telemetry signals, which command trigger signal generator 18 to emit an acoustical or optical trigger signal.

In some examples bradycardia or asystole is determined by a pacing escape interval timer expiring within a timing circuit included in control module 80. A pacing escape interval may be set in response to a sensed cardiac event signal received by control module 80 from electrical sensing module 86. In response to the pacing escape interval expiring, a control signal may be passed to TCC trigger signal generator 84 (FIG. 4A), acoustical or optical trigger signal generator 18 (FIG. 4B), or telemetry module 88. In some examples, if another cardiac event, is sensed before the pacing escape interval expires, no trigger signal is sent. The pacing escape interval is restarted upon a trigger signal or a sensed event signal. For example, in response to a P-wave sensed event signal, control module 80 may be configured to set a counter or clock to an atrioventricular (AV) interval. If an R-wave sensed event signal is received from electrical sensing module 86 prior to expiration of the AV interval, the AV interval is cancelled, and a trigger signal is not produced by sensing device 20. If the AV interval expires without receiving another cardiac sensed event signal, the trigger signal is emitted to cause the pacemaker 100 to deliver an atrial-synchronized ventricular pacing pulse upon receiving and detecting the trigger signal.

Figure 5:
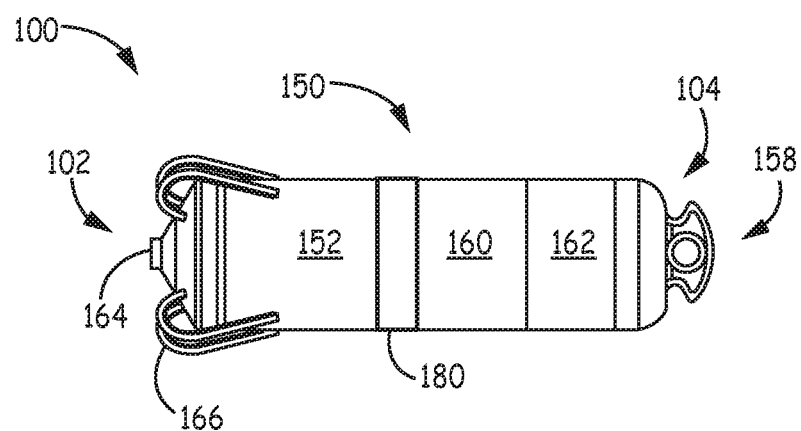
FIG. 5 is a conceptual diagram of the pacemaker of FIG. 1.

FIG. 5 is a conceptual diagram of pacemaker 100. Pacemaker 100 includes electrodes 162 and 164 spaced apart along the housing 150 of pacemaker 100. Electrode 164 is shown as a tip electrode extending from a distal end 102 of pacemaker 100, and electrode 162 is shown as a ring electrode along a mid-portion of housing 150, for example adjacent proximal end 104. In alternative embodiments, pacemaker 100 may include two or more ring electrodes or other types of electrodes exposed along pacemaker housing 150 for delivering electrical stimulation to the heart. Electrodes 162 and 164 and other electrodes described herein may be, without limitation, titanium, platinum, iridium or alloys thereof and may include a low polarizing coating, such as titanium nitride, iridium oxide, ruthenium oxide, platinum black among others. Electrodes 162 and 164 may be positioned at locations along pacemaker 100 other than the locations shown.

The housing 150 includes a control electronics subassembly 152, which houses the electronics for producing stimulation pulses and performing therapy delivery functions of pacemaker 100. As one example, control electronics subassembly 152 may include a pulse generator and a receiving transducer for receiving the trigger signal from sensing device 20 and triggering the pulse generator to deliver a pacing pulse via electrodes 162 and 164 in response to the trigger signal. In some embodiments, electrodes 162 and 164 are also used for sensing cardiac EGM signals, in which case control electronics subassembly 152 includes a sensing module.

Housing 150 further includes a battery subassembly 160, which provides power to the control electronics subassembly 152. Housing 150 is formed from a biocompatible material, such as a stainless steel or titanium alloy. In some examples, the housing 150 may include an insulating coating. Examples of insulating coatings include parylene, urethane, PEEK, or polyimide among others. The entirety of the housing 150 may be insulated, but only electrodes 162 and 164 uninsulated. In other examples, the entirety of the housing 150 may function as an electrode instead of providing a localized electrode such as electrode 162. Alternatively, electrode 162 may be electrically isolated from the other portions of the housing 150. Electrodes 162 and 164 form an anode and cathode pair for bipolar cardiac pacing.

Pacemaker 100 may include a set of active fixation tines 166 to secure pacemaker 100 to patient tissue, e.g. by piercing the endocardial tissue and/or interacting with the ventricular trabeculae. Fixation tines 166 are configured to anchor pacemaker 100 to position electrode 164 in operative proximity to a targeted tissue for delivering therapeutic electrical stimulation pulses. Numerous types of active and/or passive fixation members may be employed for anchoring or stabilizing pacemaker 100 in an implant position.

Pacemaker 100 may further include a delivery tool interface 158. Delivery tool interface 158 is located at the proximal end of pacemaker 100 and is configured to connect to a delivery device, such as a catheter, used to position pacemaker 100 at an implant location during an implantation procedure, for example within a heart chamber.

Pacemaker 100 may be configured to receive trigger signals sent from sensing device 20 in the form of TCC signals via electrodes 162 and 164 in some examples. In other examples, pacemaker 100 may include a coupling member 180 for coupling a trigger signal from sensing device 20 to a receiving transducer enclosed within housing 150. For example, coupling member 180 may be an acoustic coupling member for transferring sound waves to an acoustic receiving transducer (not shown) enclosed within housing 150 along an inner surface of coupling member 180. In another example, coupling member 180 may be a transparent window for transferring light emitted by trigger signal generator 18 to an optical receiving transducer enclosed within housing 150 along an inner surface of member 180.

Figure 6A:
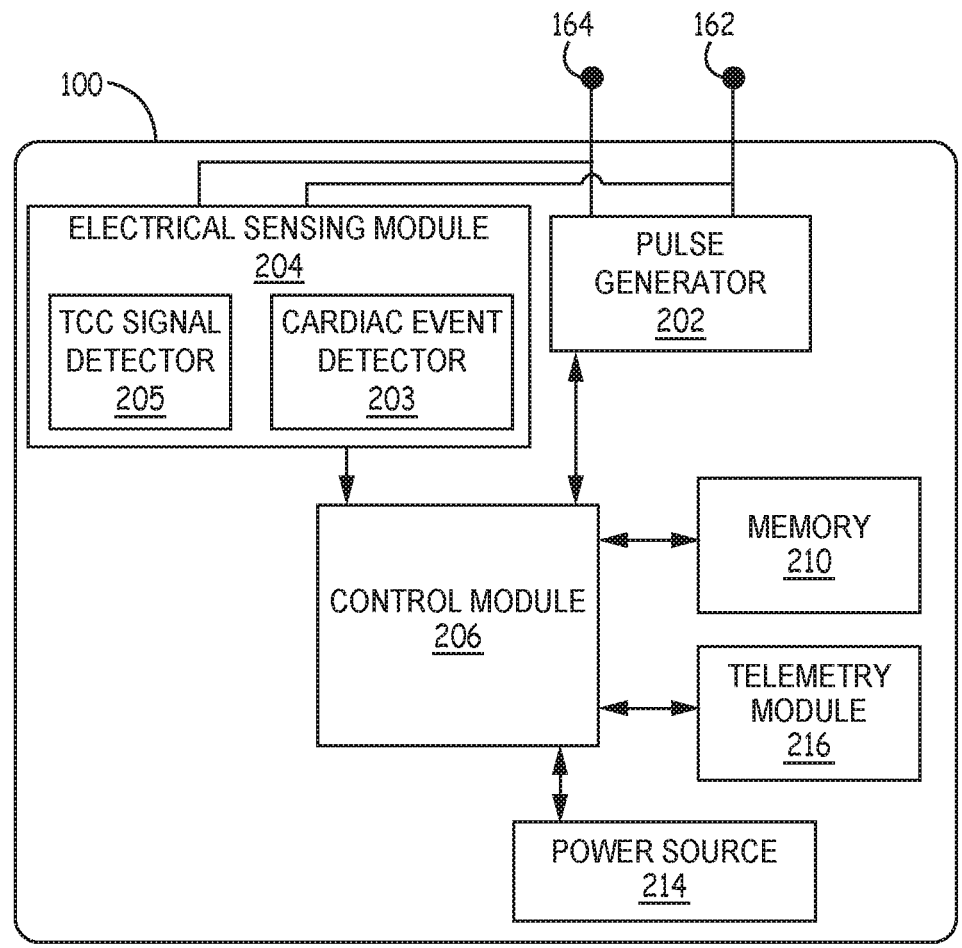
FIG. 6A is a functional block diagram of an example configuration of the pacemaker of FIG. 5.

FIG. 6A is a functional block diagram of an example configuration of pacemaker 100. Pacemaker 100 includes a pulse generator 202, a control module 206, memory 210 and a power source 214. Pacemaker 100 may include an electrical sensing module 204 for sensing cardiac events from EGM signals, e.g., ventricular R-waves, developed across electrodes 162 and 164 and/or for detecting TCC trigger signals from sensing device 20 via electrodes 162 and 164. In some examples, electrodes 162 and 164 serve as a transmitting and receiving dipole for tissue conductance communication with sensing device 20.

Figure 6B:
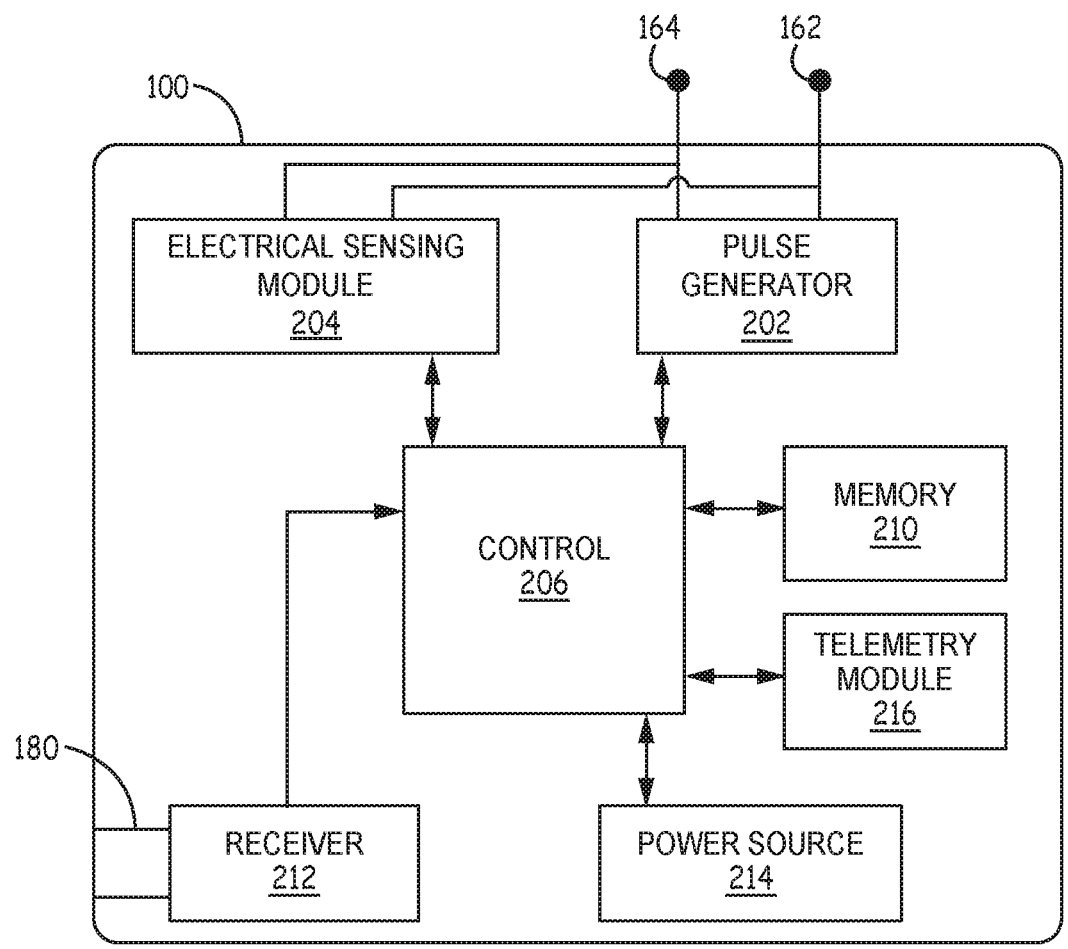
FIG. 6B is a functional block diagram of an alternative example of the pacemaker.

FIG. 6B is a functional block diagram of an alternative example of pacemaker 100. In this example, pacemaker 100 includes a trigger signal receiver 212 configured to receive and detect an optical or acoustical trigger signal sent from sensing device 20. If sensing device 20 is configured to produce trigger signals in the form of an optical or acoustical signal, receiver 212 is provided including an optical transducer or an acoustical transducer, respectively, that produces an electrical signal when an optical or acoustical trigger signal is received via coupling member 180. The electrical signal is analyzed to detect the trigger signal and a trigger detect signal is passed from receiver 212 to control module 206.

In other examples, telemetry module 216 may be configured to detect trigger signals sent from sensing device 20 in the form of wireless RF communication signals. As such, a trigger signal detector implemented in pacemaker 100 may include at least one of TCC signal detector 205, telemetry module 216 or acoustical or optical receiver 212.

Pulse generator 202 generates electrical stimulation pulses that are delivered to heart tissue via electrodes 162 and 164. Control module 206 controls pulse generator 202 to schedule a stimulation pulse in response to receiving a trigger detect signal from TCC signal detector 205, receiver 212, or telemetry module 216. In other embodiments, pulse generator 202 may be configured to deliver a stimulation pulse directly by a trigger detect signal from TCC signal detector 205, receiver 212, or telemetry module 216. For example, a switch responsive to a trigger detect signal may enable pulse generator 202 to deliver a stimulation pulse to a targeted tissue via electrodes 162 and 164.

Pulse generator 202 may include one or more capacitors and a charging circuit to charge the capacitor(s) to a pacing pulse voltage. The pacing capacitor may be charged to the pacing pulse voltage while control module 206 waits for a trigger detect signal from receiver 212 or from electrical sensing module 204 or telemetry module 216, depending on the type of trigger signal that sensing device 20 is configured to transmit to pacemaker 100. Upon detecting the trigger signal, control module 206 may control pulse generator 202 to couple the pacing capacitor to pacing electrodes 162 and 164 to discharge the capacitor voltage and thereby deliver the pacing pulse. Alternatively, detection of the trigger signal initiates pacing capacitor charging and when a predetermined pacing pulse voltage is reached, the pulse is delivered. Pacing circuitry generally disclosed in U.S. Pat. No. 8,532,785 (Crutchfield), hereby incorporated herein by reference in its entirety, may be implemented in pacemaker 100 for charging a pacing capacitor to a predetermined pacing pulse amplitude under the control of control module 206 and for delivering a pacing pulse.

Receiver 212 (FIG. 6B) may be included to receive trigger signals through coupling member 180. Receiver 212 includes one or more receiving transducers, which may be mounted directly along an inner surface of coupling member 180, e.g., for receiving sound waves or light emitted from sensing device 20. The trigger signal causes a receiving transducer to produce a voltage signal that is passed to a comparator included in receiver 212 (or control module 206) for comparison to a trigger signal detection threshold. If the voltage signal produced by the receiving transducer is greater than the detection threshold, a trigger detect signal is passed to control module 206, or directly to pulse generator 202, to cause pacing pulse delivery.

In some examples, pulse generator 202 is enabled to deliver a pacing pulse immediately upon receiving a trigger detect signal, either directly from receiver 212 or via control module 206. Alternatively, the pacing pulse may be delivered after a predetermined time delay. In either case, the system controls the delivery of a pacing pulse by pacemaker 100 to occur at a desired time interval following a sensed event. For example, sensing device 20 may sense a P-wave and a trigger signal may be sent to the pacemaker 100 at a desired AV interval less any inherent system delays to cause the pacemaker 100 to deliver a pacing pulse at the desired AV interval.

In some examples, pacemaker 100 is solely a therapy delivery device without cardiac event sensing capabilities. In other examples, pacemaker 100 may include a cardiac event detector 203 coupled to electrodes 162 and 164 for sensing EGM signals for use in controlling the delivery of pacing pulses. Cardiac event detector is configured to sense cardiac electrical events, such as R-waves and may include one or more filters, amplifiers, sense amplifiers, rectifiers, comparators, analog-to-digital converters and the like for detecting cardiac events from the intracardiac EGM signal.

For example, when pacemaker 100 is implanted in the RV, R-waves may be sensed by sensing module 204. Sensing module 204 generates an R-wave sensed event signal that is provided to control module 206. Control module 206 may start a pacing timing interval upon receiving a trigger detect signal from TCC signal detector 205, receiver 212 or telemetry module 216. If an R-wave sensed event signal is received by control module 206 prior to the pacing timing interval expiring, the pacing pulse may be withheld and no pacing pulse is delivered by pulse generator 202. If the pacing timing interval expires prior to receiving an R-wave sensed event signal from cardiac event detector 203, control module 206 enables pulse generator 202 to deliver a pacing pulse.

Power source 214 provides power to each of the other modules and components of pacemaker 100 as required. Power source 214 may include one or more energy storage devices, such as one or more rechargeable or non-rechargeable batteries. The connections between power source 214 and other pacemaker modules and components are not shown for the sake of clarity.

Circuitry represented by the block diagrams shown in FIGS. 6A and 6B may include any discrete and/or integrated electronic circuit components that implement analog and/or digital circuits capable of producing the functions attributed to pacemaker 100 herein. The functions attributed to pacemaker 100 herein may be embodied as one or more processors, hardware, firmware, software, or any combination thereof. Control module 206 may include any one or more of a microprocessor, a controller, a digital signal processor (DSP), an application specific integrated circuit (ASIC), a field-programmable gate array (FPGA), state machine, or equivalent discrete or integrated logic circuitry. Depiction of different features of pacemaker 100 as discrete modules or components is intended to highlight different functional aspects and does not necessarily imply that such modules must be realized by separate hardware or software components. Rather, functionality associated with one or more modules may be performed by separate hardware, firmware or software components, or integrated within common or separate hardware, firmware or software components, which may include combinational or sequential logic circuits, state machines, memory devices, etc.

Memory 210 may include computer-readable instructions that, when executed by a processor included in control module 206, cause control module 206 to perform various functions attributed throughout this disclosure to pacemaker 100. The computer-readable instructions may be encoded within memory 210. Memory 210 may include any non-transitory, computer-readable storage media including any volatile, non-volatile, magnetic, optical, or electrical media, such as a random access memory (RAM), read-only memory (ROM), non-volatile RAM (NVRAIVI), electrically-erasable programmable ROM (EEPROM), flash memory, or other digital media with the sole exception being a transitory propagating signal. Memory 210 stores intervals, counters, or other data used by control module 206 to control the delivery of pacing pulses by pulse generator 202 in response to detection of a trigger signal sent from sensing device 20.

In one embodiment, pacemaker 100 includes only TCC signal detector 204 or receiver 212, pulse generator 202 including low voltage charging circuitry and a pacing capacitor, power source 214 and control module 206, which may be implemented as a logic circuit for controlling pacing pulse delivery in response to trigger signal detection. The pacemaker 100 in this example is minimized in size and functionality and does not include cardiac event detector 203 for receiving physiological signals and does not include telemetry module 216 for performing RF wireless communication with sensing device 20 or external device 40.

In another example, pacemaker 100 includes a cardiac event detector 203 that is coupled to electrodes 162 and 164 for receiving an intracardiac EGM developed across electrodes 162 and 164. If pacemaker 100 receives a trigger signal from sensing device 20, and control module 206 schedules a ventricular pacing pulse in response to the trigger signal, the scheduled pacing pulse may be canceled if an R-wave sensed event signal is received by control module 206 from cardiac event detector 203 prior to pacing pulse delivery.

When included telemetry module 216 includes an antenna and transceiver for communication with external device 40 and/or sensing device 20 via bi-directional wireless RF communication signals. If sensing device 20 is configured to transmit trigger signals via telemetry module 88, pacemaker 100 receives the trigger signals via telemetry module 216. Control module 206 receives a signal from telemetry module 216 indicating that a trigger signal has been received and schedules a pacing pulse.

Control module 206 may include a timer or counter used to schedule a pacing pulse at a predetermined time interval after receiving a trigger signal, e.g., after a predetermined AV delay, which may take into account any system delays associated with sending and receiving the trigger signal after sensing device 20 senses the P-wave. In other examples, control module 206 may be configured to control pulse generator 202 to deliver the pacing pulse immediately upon receiving the trigger signal.

Pacemaker 100 may be configured to send ventricular event communication signals to sensing device 20 in some examples. As described below, pacemaker 100 may generate a ventricular event communication signal, e.g., an R-wave event signal or a ventricular pace event signal, to indicate to sensing device 20 when pacemaker 100 has sensed an R-wave or delivered a pacing pulse, respectively. Pacemaker 100 may be configured to generate ventricular event communication signals by pulse generator 202 in the form of TCC signals transmitted by electrodes 162 and 164. In this case, pulse generator 202 includes both a pacing pulse generator (e.g., one or more low voltage capacitors and associated charging circuitry) and a TCC signal generator producing a modulated carrier frequency signal as described above. The TCC signals produced by pulse generator 202 are not therapeutic pacing pulses, but are communication signals intended for detection by sensing device 20. In other examples, pacemaker 100 is configured to generate a ventricular event communication signal sent to sensing device 20 as a RF telemetry signal sent by telemetry module 216, in which case pulse generator 202 is used solely for producing pacing pulses.

As described in greater detail below, for example in conjunction with FIG. 11, in some example methods sensing device 20 may be configured to produce P-wave sense communication signals that are transmitted to pacemaker 100 to indicate when a P-wave is sensed by sensing device 20 before enabling trigger signal transmission by sensing device 20. P-wave sense communication signals may be transmitted in any of the forms that trigger signals are transmitted as described above, but may be distinct from a pacing trigger signal in form or signal pattern or characteristics so that the P-wave sense communication signal does not cause pacemaker 100 to schedule a ventricular pacing pulse. Pacemaker control module 206 may use the P-wave sense communication signal for determining a P-R interval and setting a pacing interval based at least in part on the P-R interval in some examples.

Figure 7:
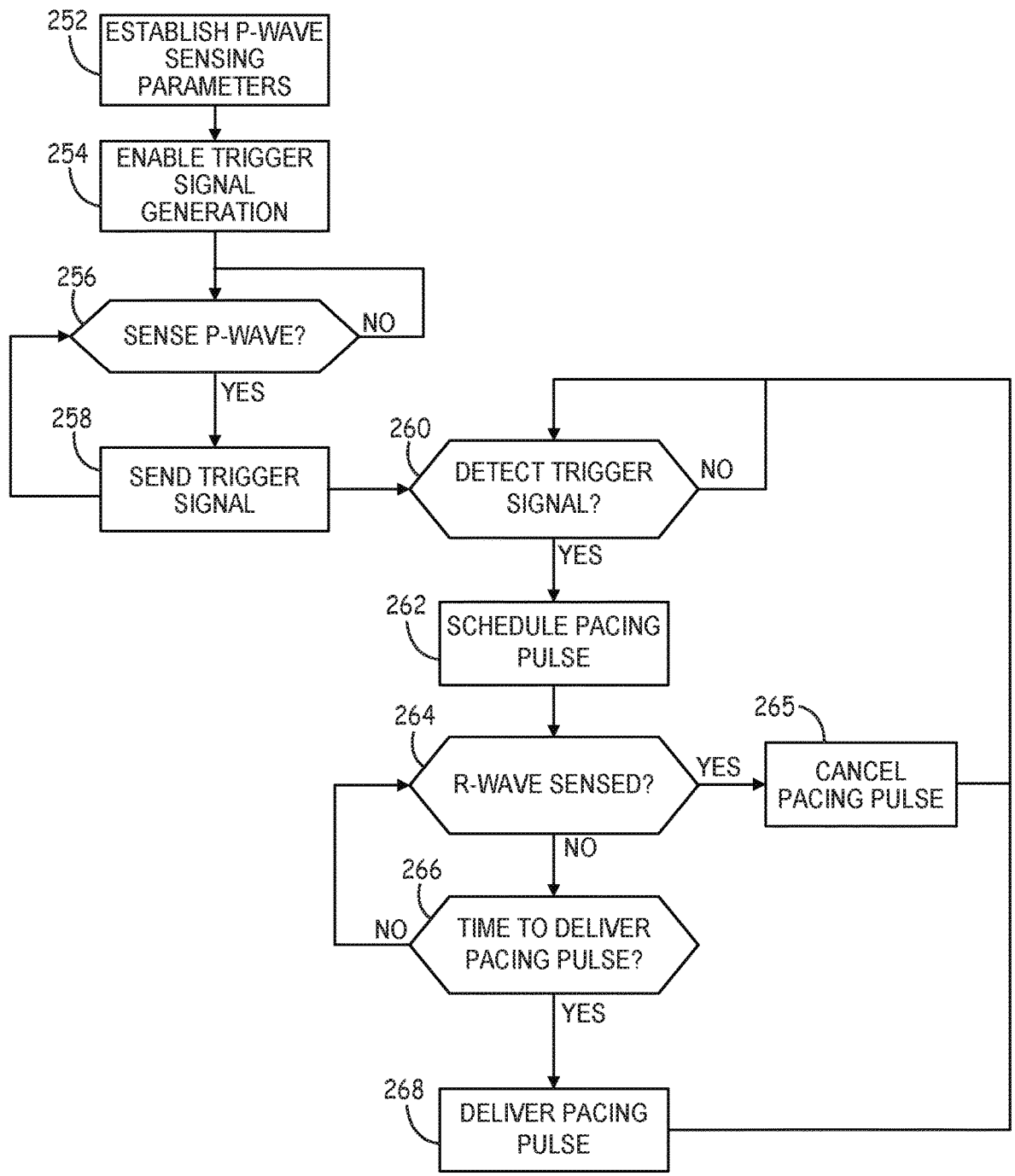
FIG. 7 is a flow chart of a method for delivering triggered pacing by the IMD system of FIG. 1 according to one example.

FIG. 7 is a flow chart 250 of a method for delivering atrial-synchronized ventricular pacing by IMD system 10 according to one example. At block 252, control module 80 of sensing device 20 establishes P-wave sensing parameters. P-wave sensing parameters may include selecting a sensing vector when more than one sensing electrode vector is available, e.g., selecting from among the vectors between electrodes 26 and 28, between electrodes 26 and 27, and between electrodes 28 and 27 as shown in FIG. 3B. Other P-wave sensing parameters established at block 252 may include sensitivity, P-wave sensing threshold, and ECG signal filtering properties. Sensing device 20 may store ECG signal episodes and P-wave sensed event markers for transmission to external device 40 for review by a clinician and confirmation of reliable P-wave sensing. P-wave sensing parameters may be programmable based on review of the ECG signal episode. During an implant procedure, review of the ECG signal and P-wave sensed event markers may enable the adjustment of the implant location of sensing device 20 within the target implant region as described above in conjunction with FIG. 2 for optimizing P-wave signal strength and reliable P-wave sensing. For example, P-wave sensing parameters may be established at block 252 when sensing device 20 is implanted superiorly to the fourth intercostal space along the right side of the patient's sternum.

After establishing P-wave sensing parameters at block 252, P-wave sensing and trigger signal generation are enabled at block 254. When a P-wave is sensed by electrical sensing module 86 at block 256, a P-wave sensed event signal is passed to control module 80. Control module 80 responds to the P-wave sensed event signal by sending a trigger signal to pacemaker 100 at block 258. In one example, the trigger signal is sent immediately to pacemaker 100 to indicate that a P-wave is sensed and that a pacing pulse is to be scheduled. In another example, the trigger signal is sent after a predetermined time interval, e.g., a predetermined AV delay interval so that the pacemaker 100 is triggered to immediately deliver the pacing pulse. After sending the trigger signal at block 258, sensing device control module 80 returns to block 256 to wait for the next P-wave sensed event.

At block 260, pacemaker 100 waits for a trigger signal from sensing device 20. Pacemaker 100 is configured to detect the trigger signal sent from sensing device 20 in accordance with the type of trigger signal sent. As discussed above, sensing module 204 may be configured to detect a TCC trigger signal received via electrodes 162 and 164 and pass a trigger signal detection signal to control module 206. In another example, telemetry module is configured to receive a trigger signal in the form of an RF telemetry signal sent by sensing device 20 and pass a trigger signal detection signal to control module 206 when a trigger signal is received. In still another example, receiver 212 may be configured to detect an optical or acoustical trigger signal as described above and pass a trigger signal detection signal to pacemaker control module 206.

When a trigger signal is detected by pacemaker 100 at block 260, pacemaker control module 206 schedules the pacing pulse at block 262. The pacing pulse may be scheduled and generated immediately upon detecting the trigger signal, e.g., on the next clock cycle. Pacemaker 100 may charge the pacing capacitor(s) included in pulse generator while waiting for the trigger signal so that the pacing pulse can be delivered without delay. In other examples, control module 206 of pacemaker 100 schedules the pacing pulse at block 262 by starting a predetermined time interval (e.g., by setting a timer or counter to count clock cycles). The predetermined time interval may be a predetermined AV delay interval so that the pacing pulse is scheduled to be delivered at the expiration of the AV delay interval after detecting the trigger signal that is sent immediately upon sensing the P-wave by sensing device 20.

If pacemaker 100 is configured to monitor an intracardiac EGM signal for intrinsic R-waves, the sensing module 204 may produce an R-wave sensed event signal during the predetermined time interval before the pacing pulse is delivered. If control module 206 receives an R-wave sensed event signal at block 264 before the scheduled pacing pulse is delivered, the scheduled pacing pulse is canceled by control module 206 at block 265. Pacemaker control module 206 determines that it is time to deliver the pacing pulse at block 266 if the predetermined time interval started at block 262 has expired. If an R-wave is not sensed before it is time to deliver the pacing pulse, as determined at block 266, the pacing pulse is delivered by pacemaker 100 at block 268 via electrodes 162 and 164. Pacemaker control module 206 returns to block 260 to wait for the next trigger signal to be detected.

If pacemaker 100 is not configured to sense cardiac electrical signals, monitoring for a sensed R-wave at block 262 is not required. Pacemaker 100 delivers the pacing pulse each time it is scheduled after detecting a trigger signal.

Figure 8:
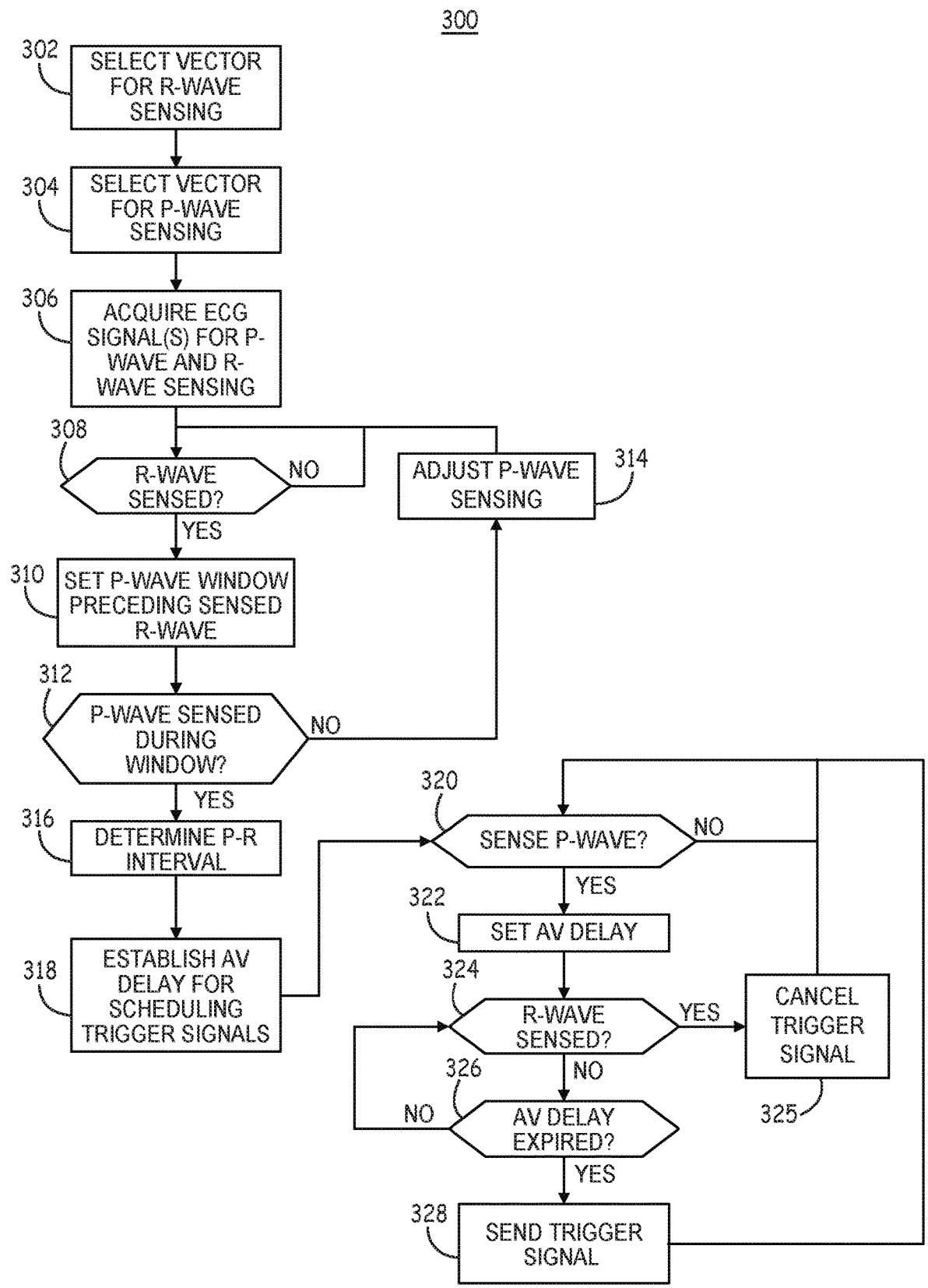
FIG. 8 is a flow chart of a method for controlling atrial-synchronized ventricular pacing according to another example.

FIG. 8 is a flow chart 300 of a method for controlling atrial-synchronized ventricular pacing delivered by IMD system 10 according to another example. The method shown in FIG. 8 for identifying P-waves is performed by the sensing device 20. At block 302, sensing device 20 selects a vector for R-wave sensing if multiple sensing vectors are available. Referring back to FIG. 3B, for example, this may be a vector between electrodes 28 and 27, between electrodes 26 and 27, or between electrodes 26 and 28. In general, sensing device 20 selects the best vector for R-wave sensing, e.g., by determining a signal-to noise ratio, noise content, or other signal quality analysis. At block 304, sensing device 20 selects a vector for P-wave sensing. In the example of FIG. 3B, this vector may be a sensing vector between electrodes 28 and 27, between electrodes 26 and 27, or between electrodes 26 and 28. The P-wave sensing vector may be selected based on a signal having the highest P-wave peak amplitude. If a single sensing vector is available, P-waves and R-waves are sensed from the same ECG signal.

At block 306, an ECG signal is received by the electrical sensing module 86 via the selected sensing vector(s). The ECG signal may be digitized and buffered to store segments of the ECG signal for analysis and review. When an R-wave is sensed by the electrical sensing module 86 at block 308, an R-wave sensed event is passed to the control module 80, which sets a P-wave sensing window preceding the R-wave at block 310. The P-wave sensing window is an interval of time preceding the sensed R-wave during which a P-wave is expected to occur based on an expected AV conduction time. At block 312, control module 80 determines if a P-wave sensed event signal was received from electrical sensing module 86 during the P-wave sensing window. If not, the P-wave sensing parameters may be adjusted automatically at block 314. In some patients, P-waves may be very low amplitude requiring manual verification by a clinician using external device 40 and sending and receiving data to sensing device 20. In this case, P-wave sensing parameters may be adjusted by a user sending programming commands by external device 40. If other sensing vectors are available, a different sensing vector may be selected. Other P-wave sensing parameters that may be adjusted include ECG signal filtering, P-wave sensing threshold and sensitivity.

Once P-waves are confirmed as being sensed within the P-wave sensing window preceding sensed R-waves, control module 80 determines the P-R interval between sensed P-waves and sensed R-waves at block 316. Sensing device 20 uses the P-R interval to set an AV delay at block 318. Typically the AV delay is set shorter than the P-R interval to promote atrial-synchronized ventricular pacing at an optimal AV delay that provides hemodynamic benefit to the patient. Generally, the AV delay is the time interval between a P-wave sensed by the sensing device 20 and a scheduled ventricular pacing pulse delivered by pacemaker 100. In the example of FIG. 7, the AV delay is the time interval between a sensed P-wave and a trigger signal that is passed to pacemaker 100 to trigger ventricular pacing pulse delivery. As such, the AV delay in this case is approximately the time between a P-wave sensed by sensing device 20 and a ventricular pacing pulse delivered by pacemaker 100 less any system delays that occur between trigger signal transmission and pacing pulse delivery.

These system delays may be negligible in some systems, e.g., less than 10 ms, and considered within an acceptable AV delay specification range. In other cases, the AV delay established at block 318 may take into account system delays that occur from the time the trigger signal is generated by sensing device 20 and the time it takes to detect the trigger signal by pacemaker 100 and generate and deliver a pacing pulse. The AV delay established at block 318 may be shortened from the desired actual AV delay between a sensed P-wave and a delivered pacing pulse by the anticipated system delays associated with trigger signal transmission and detection.

After establishing reliable P-wave sensing and the AV delay at blocks 312 through 318, the IMD system 10 enters a therapeutic pacing mode by starting the AV delay at block 322 in response to sensing a P-wave at block 320. Setting the AV delay schedules a trigger signal to be passed to pacemaker 100. If an R-wave sensed event signal is received by sensing device control module 80 from electrical sensing module 86 during the running AV delay interval, i.e., prior to expiration of the AV delay interval, the scheduled trigger signal is cancelled at block 325. The control module 80 waits for the next P-wave sensed event signal at block 320.

If the AV delay expires at block 326 without an R-wave sensed event signal being produced by sensing module 86 during the AV delay, the sensing device control module 80 produces a trigger signal at block 328. As described above, the trigger signal may be an electrical TCC signal produced by TCC trigger signal generator 84 and transmitted via electrodes 26, 27 and/or 28; an RF telemetry signal transmitted by telemetry module 88; or an optical or acoustical trigger signal produced by trigger signal generator 18. After sending the trigger signal to pacemaker 100, sensing device 20 returns to block 320 to wait for the next P-wave.

In some examples, sensing device 20 may be configured to detect the signal artifact caused by delivery of a ventricular pacing pulse delivered by pacemaker 100. Accordingly, in some embodiments, sensing the P-wave at block 320 may include applying additional P-wave verification criteria in addition to detecting a P-wave sensing threshold crossing. For example, if a pacing artifact is detected and a "sensed P-wave" is within a predetermined time interval of the pacing artifact, e.g., within 20 ms, the peak amplitude of the "sensed P-wave" may be compared to a maximum amplitude threshold. If the peak amplitude is greater than the maximum amplitude threshold and/or within the predetermined time interval of the pacing pulse artifact, a P-wave is not sensed at block 320. A P-wave sensing threshold crossing detected by sensing module 86 may be rejected as a sensed P-wave based on the additional P-wave sensing criteria relating to a maximum peak amplitude limit and/or its timing relative to a pacing pulse artifact detected by electrical sensing module 86 from the ECG signal.

Figure 9:
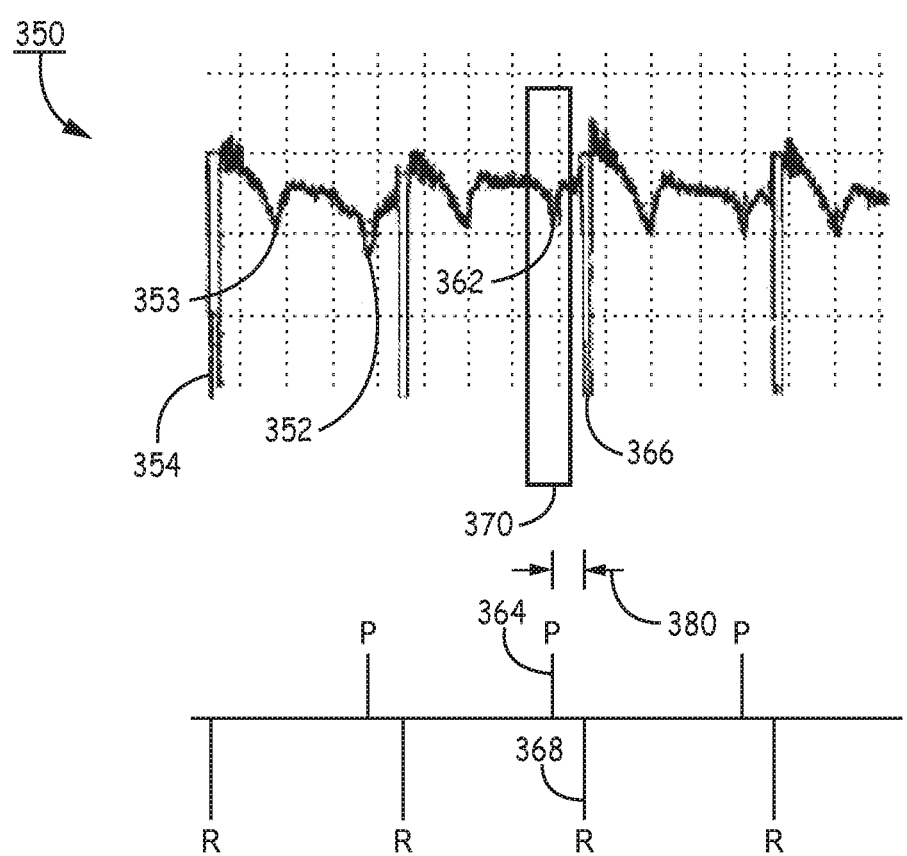
FIG. 9 depicts an electrocardiogram (ECG) that may be recorded by the sensing device of FIG. 1.

FIG. 9 depicts an ECG signal 350 that may be produced and recorded by sensing device 20. The ECG includes P-waves 352, T-waves 353, and much larger-amplitude R-waves 354 and 366. When sensing module 86 senses a P-wave 362, a P-wave sensed event signal 364 is passed to control module 80. When sensing module 86 senses R-wave 366, an R-wave sensed event signal 368 is passed to control module 80. In response to the R-wave sensed event signal 368, control module 80 may set a P-wave sensing window 370 preceding the R-wave sensed event signal 368. P-wave sensing window 320 may extend, for example from 20 ms before the R-wave to 300 ms before the R-wave 366 and may depend on the heart rate (e.g., the R-R interval). If a P-wave sensed event signal 364 occurs during the P-wave sensing window 370, P-wave sensing is verified. The P-R interval 380 may be used in setting an AV delay that is used to control trigger signal transmission times as described in conjunction with FIG. 8. In some examples, sensing device 20 may also be configured to sense pacing-evoked R-waves or pacing pulses delivered by pacemaker 100, which may allow for enhanced timing of pacing pulses following sensed P-waves.

It is recognized that control module 80 may additionally or alternatively be configured to set an R-wave sensing window following a P-wave sensed event signal 364. If an R-wave sensed event signal occurs during the R-wave sensing window, the P-wave sensed event signal is deemed valid. This verification of P-wave sensed event signals relative to R-wave sensed event signals based on a sensing window set according to an expected P-R interval range (or AV conduction time) may verify that T-waves 353 are not being oversensed as P-waves 352.

Figure 10:
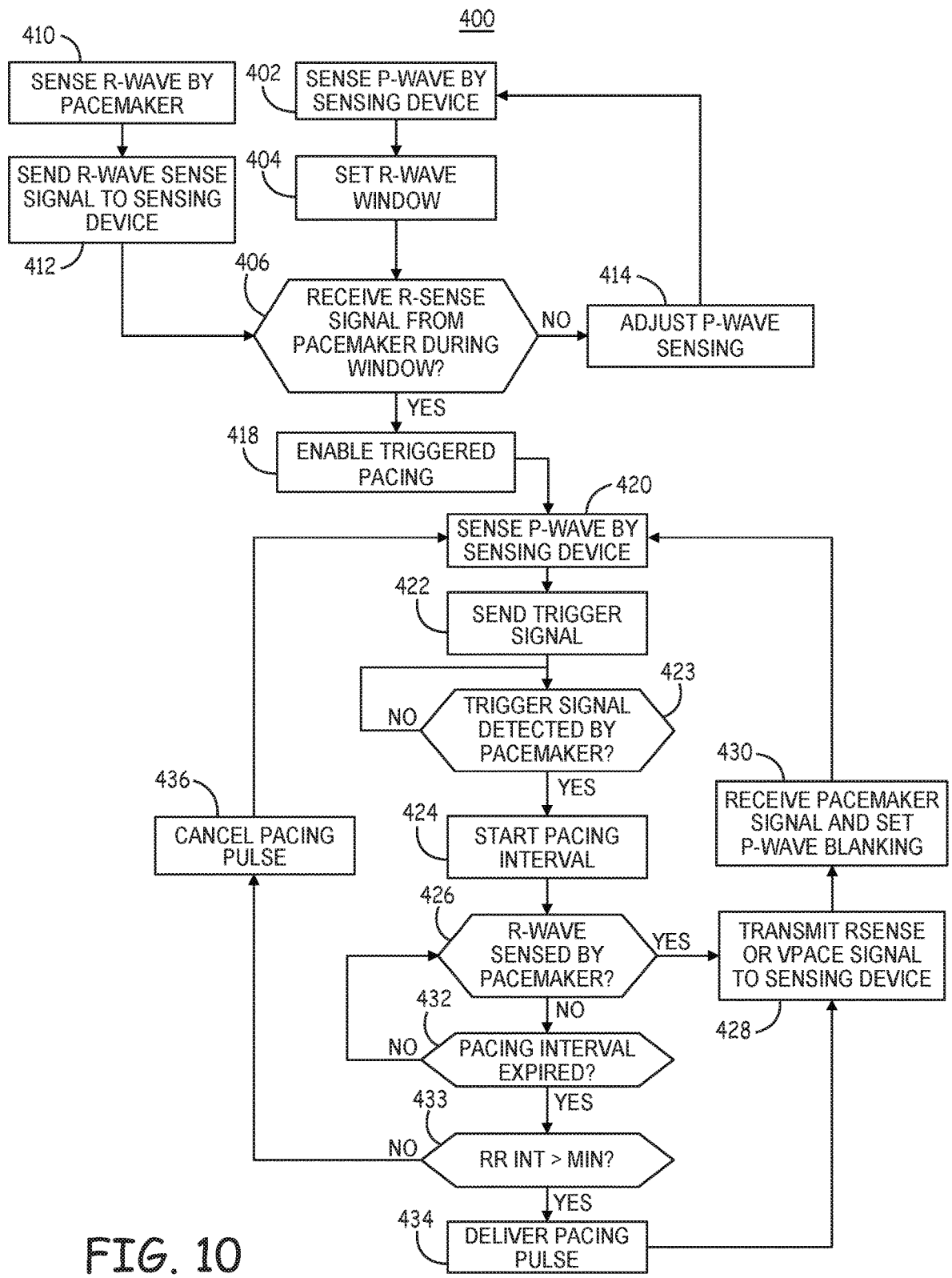
FIG. 10 is a flow chart of a method for controlling and delivering atrial-synchronized ventricular pacing according to another example.

FIG. 10 is a flow chart 400 of a method for controlling and delivering atrial-synchronized ventricular pacing by IMD system 10 according to another example. In this example, sensing device 20 is not required to sense both P-waves and R-waves. The implant location of sensing device 20 may be optimized for sensing P-waves as described above in conjunction with FIG. 2. For example, an implant location of sensing device 20 may be selected in the targeted implant area marked by boundary 50 where the P-wave signal amplitude is maximized or relatively high compared to other locations and the R-wave signal amplitude is minimized or relatively low compared to other locations. For example, sensing parameters for optimal P-wave sensing may be established when sensing device is implanted superior to the fourth intercostal space and on the right side of the patient's sternum. Additionally, the orientation of sensing device 20 may be selected to optimize P-wave sensing. If more than one sensing vector is available, the optimal P-wave sensing vector is selected.

When a P-wave is sensed by sensing device 20 at block 402, control module 80 sets an R-wave window at block 404 in response to the P-wave sensed event signal from sensing module 86. Pacemaker 100 is configured to sense R-waves from the intraventricular EGM signal. When pacemaker 100 senses an R-wave at block 410, the pacemaker control module 206 transmits an R-wave sensed event communication signal to sensing device 20 at block 412. This R-wave sensed event signal may be a TCC communication signal transmitted using pacemaker electrodes 162 and 164 or an RF telemetry signal transmitted via telemetry module 216.

If sensing device 20 does not receive an R-wave sensed event communication signal from pacemaker 100 during the R-wave window, as determined at block 406, sensing device control module 80 may adjust the P-wave sensing parameters used by sensing module 86 at block 414. If sensing device 80 does receive an R-wave sensed event signal during the R-wave window at block 406, triggered pacing is enabled at block 418. It is recognized that before enabling triggered pacing at block 418, receipt of an R-wave sensed event communication signal during the R-wave window following a sensed P-wave may be required for multiple cardiac cycles, e.g., at least three consecutive cardiac cycles, before sensing device 20 enables triggered pacing.

Once triggered pacing is enabled at block 418, sensing device 20 sends a trigger signal to pacemaker 100 at block 422 in response to sensing the next P-wave at block 420. The pacemaker 100 detects the trigger signal at block 423. Pacemaker control module 206 schedules a pacing pulse by starting a pacing interval in response to the detected trigger signal at block 424. The pacing interval may be a predetermined AV delay that may be programmed by a clinician.

If the pacemaker control module 206 receives an R-wave sensed event signal from the pacemaker electrical sensing module 204 at block 426, before the pacing interval expires, the pacemaker 100 transmits an R-wave sensed event communication signal (Rsense) to sensing device 20 at block 428. If the pacing interval does expire at block 432, without an R-wave sensed event signal produced by pacemaker sensing module 204, pacemaker control module 206 controls pulse generator 202 to deliver a pacing pulse at block 434.

It is recognized that pacemaker 100 may apply additional criteria in deciding whether to deliver or cancel a scheduled pacing pulse at block 434 after the pacing interval has expired at block 432. For example, at block 433, pacemaker control module 206 may determine the RR interval that will result from delivering the scheduled pacing pulse. In other words, control module 206 may determine the interval from the preceding R-wave sensed event signal or the preceding ventricular pacing pulse, whichever is most recent, to the scheduled ventricular pacing pulse. If this interval is less than a minimum RR interval that defines a maximum ventricular rate, the scheduled pacing pulse may be cancelled at block 436. Pacemaker 100 waits for the next trigger signal from sensing device 20. In this way, a pacemaker-mediated tachycardia is avoided.

When the pacing interval expires at block 432 and any other pacing pulse delivery criteria are met at block 433 so that scheduled pacing pulse is delivered at block 434, pacemaker 100 transmits a ventricular pace communication signal (Vpace) to sensing device 20 at block 428. In some examples, the Rsense and Vpace signals sent by pacemaker 100 are the same signal, indistinguishable from each other. In other words, pacemaker 100 may be configured to transmit an event signal at block 428 whenever an R-wave is sensed by the pacemaker 100 and whenever a pacing pulse is delivered. Sensing device 20 may respond to the event signal received from pacemaker 100 by setting a P-wave blanking interval at block 430. The P-wave blanking interval may be 100 to 300 ms long. Sensing module 86 is disabled from sensing P-waves during the P-wave blanking interval.

By setting a P-wave blanking interval following an event signal from pacemaker 100, oversensing of R-waves (such as evoked R-waves following a pacing pulse) and oversensing of T-waves as false P-waves by sensing device 20 may be avoided.

In other examples, pacemaker 100 may be configured to transmit distinct Rsense communication signals when an R-wave is sensed and Vpace communication signals when a pacing pulse is delivered. Sensing device 100 may respond to both signals by setting a P-wave blanking interval at block 430. Sensing device 100 may store Rsense and Vpace data for transmission to external device 40 to enable a clinician to review the pacing history of IMD system 10.

Figure 11:
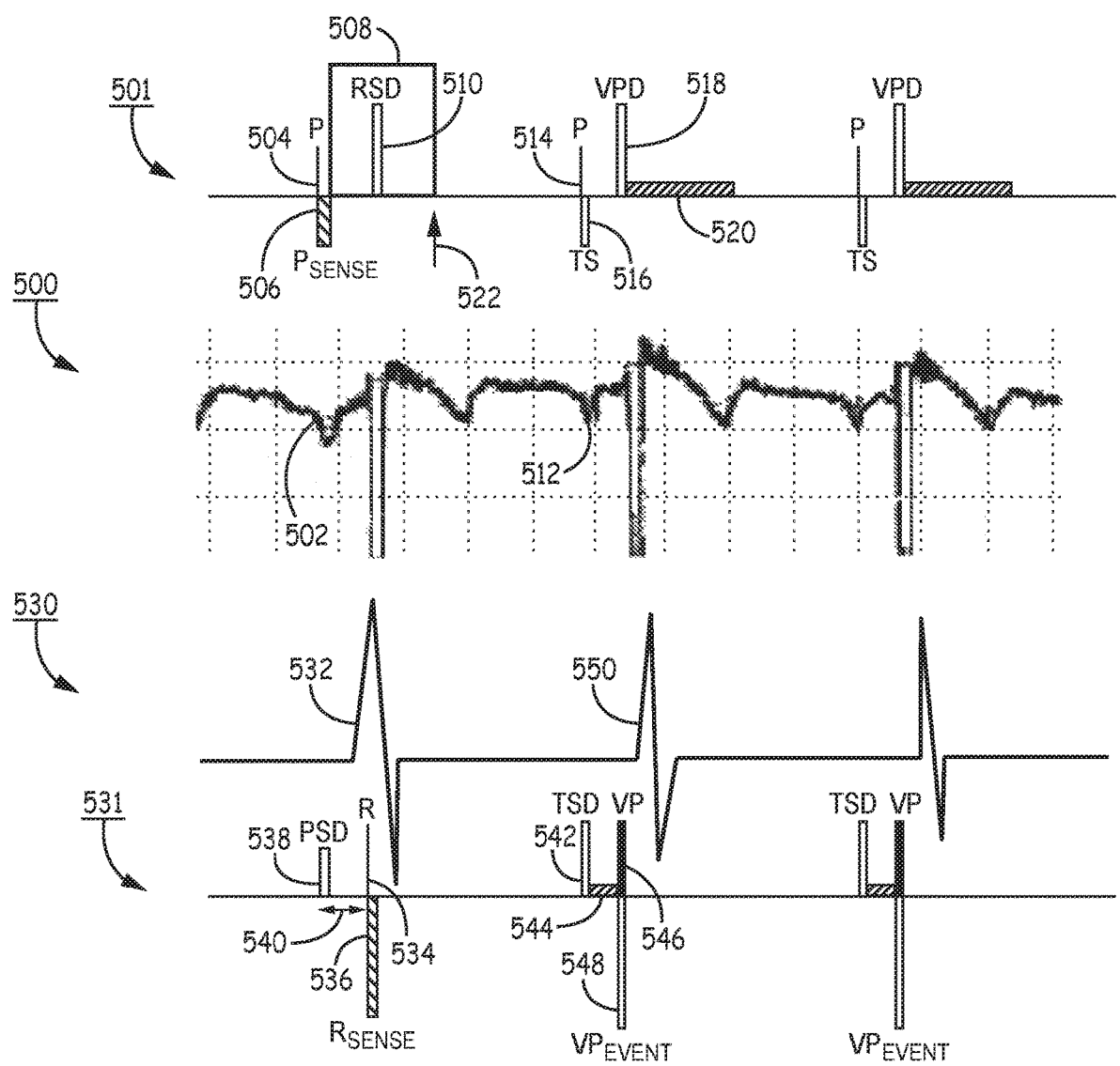
FIG. 11 depicts an ECG signal that may be acquired by the sensing device and an intraventricular EGM signal that may be acquired by the pacemaker of the IMD system of FIG. 1.

FIG. 11 depicts an ECG signal 500 that may be produced by sensing device 20 from cardiac electrical signals received via electrodes 26, 27 and/or 28 and an intraventricular EGM signal 530 that may be produced by pacemaker 100 from cardiac electrical signals received via pacemaker electrodes 162 and 164. ECG signal 500 includes P-waves 502 as well as T-waves and R-waves. ECG signal 500 may be filtered, amplified, rectified and blanked at appropriate times to enhance P-waves and suppress or reject of T-waves and R-waves to promote reliable P-wave sensing by sensing device 20. R-waves 532 are predominant in EGM signal 530 and are reliably sensed by pacemaker 100.

Signal line 501 represents signals produced by sensing device 20 in response to sensing P-waves, detecting communication signals from pacemaker 100 and generating trigger signals. Upward-going signals along signal line 501 represent signals produced by sensing device 20 and are used by sensing device control module 80 to control sensing device functions. Upward-going signals include P-wave sensed event signals 504 and 514 produced by sensing module 86. Upward-going signals may also include detection signals 510 and 518 produced upon detecting an Rsense or Vpace event communication signal, respectively, sent from pacemaker 100. In this example, detection of an Rsense event communication signal is denoted by RSD signal 510. Detection of a Vpace event communication signal is denoted by VPD signal 518. Downward-going signals along signal line 501 represent signals transmitted from sensing device 20 to pacemaker 100, such as a Psense communication signal 506 and pacing trigger signals 516.

Signal line 531 represents signals produced by pacemaker 100 in response to sensing R-waves and detecting communication signals from sensing device 20 and signals transmitted to sensing device 20 from pacemaker 100. Upward-going signals along signal line 531 represent signals produced by pacemaker 100 that are used by pacemaker control module 206 to control pacemaker functions. Upward-going signals include R-wave sensed event signals 534 produced by sensing module 204 and trigger signal detection (TSD) signals 542 produced by pacemaker 100 upon detecting a trigger signal from pacemaker 100. Upward-going signals may also include Psense detection (PSD) signals 538 produced upon detecting a Psense communication signal 506 sent from sensing device 20 before triggered pacing is enabled. Downward-going signals along signal line 501 represent signals transmitted from pacemaker 100 to sensing device 20, such as a Rsense communication signal 536 and Vpace communication signal 548.

As described in conjunction with the flow chart 400, sensing device 20 may initially verify reliable P-wave sensing before enabling triggered pacing. In response to sensing P-wave 502, sensing module 86 of sensing device 20 produces P-wave sensed event signal 504 which is passed to sensing device control module 80. Sensing device control module 80 starts an R-wave window 508 in response to receiving the P-wave sensed event signal 504 from sensing module 86.

Pacemaker 100 senses R-wave 532 and pacemaker sensing module 204 produces R-wave sensed event signal 534. Pacemaker control module 206 transmits an Rsense communication signal 536 to sensing device 20. Sensing device 20 detects the Rsense signal 536, and an Rsense detect (RSD) signal 510 is produced, e.g., by TCC signal detector 94 or telemetry module 88 depending on how pacemaker 100 is configured to transmit the Rsense signal 536, e.g., either by pulse generator 202 as a TCC signal or by telemetry module 216 as an RF communication signal, respectively. Sensing device control module 80 receives the RSD signal 510 and determines if it occurred during R-wave window 508. Upon confirming that RSD signal 510 occurs during the R-wave window 508 following P-wave sensed event signal 504, sensing device control module 80 enables triggered pacing as indicated by arrow 522.

In some examples, sensing device 20 does not transmit signals to pacemaker 100 until after triggered pacing is enabled. After triggered pacing is enabled, sensing device 20 sends a trigger signal (TS) 516 when control module 80 receives P-wave sensed event signal 514 produced by sensing module 86 in response to P-wave 512. In other examples, sensing device 20 may send Psense communication signals 506 to pacemaker 100 before triggered pacing is enabled at block 522. Psense communication signal 506 may be a TCC signal, RF communication signal, or an acoustical or optical signal produced by sensing device 20. Psense communication signal 506 is distinct from pacing trigger signals 516. Psense communication signal 506 may be distinct by being transmitted in a different form. For example, if trigger signals 516 are sent as TCC signals, Psense communication signal 506 may be transmitted as an RF communication signal. Pacemaker telemetry module 216 may be configured to "listen" for Psense communication signals if a trigger signal has not been detected for a period of time. After trigger signal 516 is received, pacemaker 100 may conserve power by reducing how often telemetry module 216 "listens" for RF communication signals.

Psense signal 506 may alternatively be the same form as the pacing trigger signals 516 (e.g., a TCC signal, RF communication signal, optical signal or acoustical signal) but have different signal features, such as a different signal amplitude, signal width, frequency or other signal characteristic distinguishable from trigger signal 516. If sensing device 20 is configured to send Psense communication signal 506, pacemaker 100 is configured to detect the Psense communication signal 506 using appropriate techniques based on the type of Psense communication signal 506 being sent. For example, pacemaker telemetry module 216, sensing module 204, or receiver 212 may detect the Psense communication signal 506 as an RF communication signal, TCC signal, or acoustical or optical signal, respectively. If Psense communication signal 506 is the sent in the same form as trigger signal 516, pacemaker 100 is configured to discriminate between Psense communication signal 506 and trigger signal 516 based on a known signal characteristic difference. The respective sensing module 204, telemetry module 216, or receiver 212 configured to detect Psense communication signal 506 produces a Psense detect (PSD) signal 538 passed to pacemaker control module 206.

In response to PSD signal 538, pacemaker control module 206 may determine the P-R interval 540 using the PSD signal 538 and R-wave sensed event signal 534 (from one or more cardiac cycles). Pacemaker control module 206 may set the pacing interval 544 as an AV interval that is shorter than the determined PR interval 540. In other examples, pacing interval 544 is programmed by a user using external device 40.

After triggered pacing is enabled at block 522, pacemaker 100 detects trigger signal 516 sent by sensing device 20. Pacemaker 100 is configured to detect trigger signal 516 according to the type of signal sent, e.g., a TCC signal detected by sensing module 204, an RF communication signal detected telemetry module 216, or an acoustical or optical signal detected by receiver 212. Upon detecting trigger signal 516, a trigger signal detect (TSD) signal 542 is passed to pacemaker control module 206. Pacemaker control module 206 sets pacing interval 544 in response to TSD signal 542. If pacing interval 544 expires without pacemaker control module 206 receiving an R-wave sensed event signal from sensing module 204, control module 206 controls pulse generator 202 to deliver ventricular pacing pulse (VP) 546. Pacemaker control module 206 may also control pacemaker 100 to transmit a Vpace event communication signal 548 to sensing device 20. Vpace event communication signal 548 may be the same as Rsense event communication signal 536 or distinct from Rsense communication signal 536. For example, Rsense communication signal 536 and Vpace event signal 548 may be sent using different modalities (TCC or RF wireless communication) or sent by the same modality but using different signal characteristics, such as signal amplitude, signal width, frequency, etc.

Sensing device 20 is configured to detect the Vpace event communication signal 548 and produce a Vpace detect (VPD) signal 518, e.g., by TCC signal detector 94 or by telemetry module 88, whichever is configured to detect VPD signal 518. Sensing device control module 80 receives the VPD signal 518 and sets a P-wave blanking interval 520 to inhibit P-wave sensing during blanking interval 520, when evoked R-wave 550 and a subsequent T-wave are expected to occur. In this way, reliable sensing of P-waves by sensing device 20 during triggered pacing and appropriate timing of trigger signals 516 sent to pacemaker 100 by sensing device 20 are achieved so that the patient may benefit from atrial-synchronized ventricular pacing provided by IMD system 10.

Thus, various examples of a medical device system and associated methods for providing atrial-synchronized ventricular pacing have been described according to illustrative embodiments. While the disclosure is susceptible to various modifications and alternative forms, specific embodiments thereof have been shown by way of example in the drawings and are herein described in detail. It should be understood, however, that the description herein of specific embodiments is not intended to limit the disclosure to the particular forms disclosed, but on the contrary, the intention is to cover all modifications, equivalents, and alternatives falling within the spirit and scope of the disclosure as defined by the appended claims.

For example, the following Items are illustrative of further embodiments: Item 1. A method for providing pacing stimuli to a heart of a patient, the method comprising: sensing a P-wave by an implantable sensing device having housing-based electrodes, the P-wave sensed via the housing-based electrodes when the implantable sensing device is implanted outside the cardiovascular system; generating a trigger signal by the sensing device in response to sensing the P-wave; detecting the trigger signal by an intracardiac pacemaker; and scheduling a ventricular pacing pulse by the intracardiac pacemaker in response to the detected trigger signal.

Item 2. The method of item 1, further comprising: detecting an R-wave by the sensing device via the housing-based electrodes; setting a P-wave sensing window in response to detecting the R-wave; verifying sensing of a preceding P-wave by the sensing device in response to sensing the preceding P-wave during the P-wave sensing window; and enabling the sending of the trigger signal in response to verifying the sensing of the preceding P-wave.

Item 3. The method of any one of items 1-2, wherein detecting the R-wave by the sensing device comprises: sensing the R-wave by the pacemaker; sending a wireless signal from the pacemaker to the sensing device in response to sensing the R-wave; and detecting the wireless signal by the sensing device.

Item 4. The method of any one of items 1-3, further comprising automatically adjusting a P-wave sensing control parameter by the sensing device in response to not sensing the preceding P-wave during the P-wave window.

Item 5. The method of any one of items 1-4, further comprising: determining, by the sensing device, a P-R interval between the preceding sensed P-wave and the detected R-wave; setting a pacing interval based at least in part on the P-R interval; and scheduling the trigger signal to be sent from the sensing device to the pacemaker at the expiration of the pacing interval.

Item 6. The method of any one of items 1-5, further comprising: detecting a second R-wave during the pacing interval by the sensing device; and cancelling the trigger signal in response to detecting the second R-wave during the pacing interval.

Item 7. The method of any one of items 1-6, wherein detecting the second R-wave comprises one of: sensing the second R-wave by the sensing device, and sensing the second R-wave by the pacemaker, transmitting an R-wave signal by the pacemaker to the sensing device in response to sensing the second R-wave, detecting the R-wave signal by the sensing device.

Item 8. The method of any one of items 1-7, further comprising: scheduling the pacing pulse by setting a pacing interval by the pacemaker in response to detecting the trigger signal; cancelling the scheduled pacing pulse if an R-wave is sensed by the pacemaker during the pacing interval; delivering the pacing pulse in response to the pacing interval expiring if an R-wave is not sensed by the pacemaker during the pacing interval;

Item 9. The method of any one of items 1-8, further comprising: sending a wireless ventricular event signal to the sensing device from the pacemaker in response to at least one of the R-wave sensed by the pacemaker during the pacing interval and the pacing pulse; detecting the ventricular event signal by the sensing device; and setting a P-wave blanking interval by the sensing device in response to detecting the ventricular event signal.

Item 10. The method of any one of items 1-10, further comprising: sensing a preceding P-wave by the sensing device; setting an R-wave window by the sensing device; sensing an R-wave by the pacemaker; sending an R-wave signal from the pacemaker to the sensing device in response to sensing the R-wave; detecting the R-wave signal by the sensing device; enabling the trigger signal to be sent by the sensing device in response to the sensing device detecting the R-wave signal during the R-wave window.

Item 11. The method of any one of items 1-10, further comprising: sending a P-wave signal from the sensing device to the pacemaker in response to sensing the preceding P-wave; determining a P-R interval by the pacemaker; and scheduling the ventricular pacing pulse by setting a pacing interval based at least in part on the P-R interval.

Item 12. The method of any one of items 1-11, further comprising: determining by the pacemaker an RR interval from one of a preceding R-wave sensed by the pacemaker and a preceding ventricular pacing pulse to the scheduled pacing pulse; comparing the RR interval to a minimum interval; and cancelling the scheduled pacing pulse in response to the RR interval being less than the minimum RR interval.

Item 14. An implantable medical device system, comprising: an extracardiac sensing device comprising: a housing; a plurality of housing-based electrodes; a sensing module enclosed by the housing and configured to sense a P-wave attendant to an atrial activation of a patient's heart via the housing-based electrodes when the sensing device is implanted outside the cardiovascular system; a trigger signal generator; and a control module configured to control the trigger signal generator to transmit a trigger signal in response to the sensing module sensing the P-wave; and an intracardiac pacemaker comprising; a trigger signal detector; a pacing pulse generator; and a control module configured to schedule a pacing pulse in response to the trigger signal detector detecting the trigger signal.

Item 15. The system of item 14, wherein the sensing device control module is further configured to: detect an R-wave attendant to a ventricular depolarization of the heart; set a P-wave sensing window in response to detecting the R-wave; verify sensing of a preceding P-wave in response to sensing the preceding P-wave during the P-wave sensing window; and enable the sending of the trigger signal in response to verifying the sensing of the preceding P-wave.

Item 16. The system of any one of items 14-15, wherein: the pacemaker further comprises: a sensing module configured to sense the R-wave; a wireless signal generator configured to transmit a wireless signal in response to the sensing module sensing the R-wave; and the sensing device comprises a signal detector configured to detect the R-wave by detecting the wireless signal by the sensing device.

Item 17. The system of any one of items 14-16, wherein the sensing device control module is further configured to automatically adjust a P-wave sensing control parameter in response to not sensing the preceding P-wave during the P-wave window.

Item 18. The system of any one of items 14-17, wherein the sensing device control module is further configured to: determine a P-R interval between the preceding sensed P-wave and the detected R-wave; set a pacing interval based at least in part on the P-R interval; and schedule the trigger signal to be sent at the expiration of the pacing interval.

Item 19. The system of any one of items 14-18, wherein the sensing device control module is further configured to: detect a second R-wave during the pacing interval; and cancel the trigger signal in response to detecting the second R-wave during the pacing interval.

Item 20. The system of any one of items 14-19, wherein: the pacemaker further comprises: a sensing module configured to sense the second R-wave; a wireless signal generator configured to transmit a wireless signal in response to the pacemaker sensing module sensing the R-wave; and the sensing device further comprises a signal detector configured to detect the second R-wave by detecting the wireless signal by the sensing device.

Item 21. The system of any one of items 14-20, wherein: the pacemaker further comprises a sensing module configured to sense an R-wave; the pacemaker control module is further configured to: schedule the pacing pulse by setting a pacing interval in response to detecting the trigger signal; cancel the scheduled pacing pulse if an R-wave is sensed by the pacemaker during the pacing interval; deliver the pacing pulse in response to the pacing interval expiring if an R-wave is not sensed by the pacemaker sensing module during the pacing interval;

Item 22. The system of any one of items 14-21, wherein: the pacemaker further comprises a ventricular event signal generator configured to send a wireless ventricular event signal to the sensing device in response to at least one of the R-wave sensed during the pacing interval and the pacing pulse; the sensing device further comprising a signal detector configured to detect the ventricular event signal; the sensing device control module is further configured to set a P-wave sensing blanking interval in response to detecting the ventricular event signal.

Item 23. The system of any one of items 14-22, wherein: the pacemaker further comprises: a sensing module configured to sense an R-wave; a signal generator configured to send an R-wave signal from the pacemaker to the sensing device in response to the pacemaker sensing module sensing the R-wave; the sensing device further comprising a signal detector configured to detect the R-wave signal sent by the pacemaker; and the sensing device control module further configured to: set an R-wave window in response to a preceding P-wave sensed by the sensing module of the sensing device; and enable the trigger signal to be sent in response to the R-wave signal being detected during the R-wave window.

Item 24. The system of any one of items 14-23, wherein: the sensing device is further configured to send a P-wave signal from the sensing device to the pacemaker in response to sensing the preceding P-wave; the pacemaker further comprises a signal detector configured to detect the P-wave signal; the pacemaker control module configured to: determine a P-R interval in response to the detected P-wave signal; and schedule the ventricular pacing pulse by setting a pacing interval based at least in part on the P-R interval.

Item 25. The system of any one of items 14-24, wherein: the plurality of housing-based electrodes comprises a first pair of electrodes defining a first sensing vector and a second pair of electrodes defining a second sensing vector, the second sensing vector at an angle of at least 45 degrees to the first sensing vector; the sensing module configured to select one of the first sensing vector and the second sensing vector for sensing the P-wave.

Item 26. The system of any one of items 14-25, wherein the sensing module senses the P-waves when the sensing device is implanted above the fourth intercostal space.

Item 27. The system of any one of items 14-26, wherein the pacemaker control module is further configured to: determine an RR interval from one of a preceding R-wave sensed by the pacemaker and a preceding ventricular pacing pulse to the scheduled pacing pulse; compare the RR interval to a minimum interval; and cancel the scheduled pacing pulse in response to the RR interval being less than the minimum RR interval.

Item 28. The system of any one of items 14-27, wherein the housing of the sensing device is an angular housing comprising a bend and the housing-based electrodes comprise a first electrode along a first end of the angular housing, a second electrode along a second end of the angular housing, and a third electrode along the bend; wherein the sensing module is configured to: sense the P-wave by a first pair of the housing-based electrodes defining a first sensing vector angle; and detecting the R-wave from a cardiac electrical signal received by a second pair of the housing-based electrodes different than the first pair and defining a second sensing vector angle that is different than the first sensing vector angle.

Item 29. An implantable, extracardiac sensing device, comprising: a housing; a plurality of housing-based electrodes; a sensing module configured to sense cardiac electrical events via the housing-based electrodes when the extracardiac sensing device is implanted outside a patient's cardiovascular system; a trigger signal generator configured to transmit a wireless trigger signal to an intracardiac pacemaker to cause the pacemaker to deliver a cardiac pacing pulse; a signal detector configured to detect a wireless event signal transmitted to the sensing signal detector by the intracardiac pacemaker; and a control module coupled to the sensing module, the trigger signal generator and the signal detector and configured to: control the trigger signal generator to generate the wireless trigger signal in response to the sensing module sensing a cardiac electrical event; set a blanking interval to inhibit sensing a next cardiac electrical event during the blanking interval in response to the signal detector detecting the wireless event signal transmitted by the intracardiac pacemaker.

Item 30. A non-transitory computer readable storage medium storing instructions which, when executed by a control module of an extracardiac sensing device and a control module of an intracardiac pacemaker of an implantable medical device system, cause the system to: sense a P-wave attendant to an atrial depolarization of the heart by the sensing device via housing-based electrodes carried by the sensing device when the sensing device is implanted outside a patient's cardiovascular system; send a trigger signal from the sensing device to the intracardiac pacemaker; detect the trigger signal by the pacemaker; and schedule a ventricular pacing pulse by the intracardiac pacemaker in response to the detected trigger signal.

The invention claimed is:

1. A method for providing pacing stimuli to a heart of a patient, the method comprising:
   sensing a P-wave by an implantable sensing device having housing-based electrodes, the P-wave sensed via the housing-based electrodes;
   generating a trigger signal by the sensing device in response to sensing the P-wave;
   detecting the trigger signal by an intracardiac pacemaker; and
   scheduling a ventricular pacing pulse by the intracardiac pacemaker in response to the detected trigger signal.

2. The method of claim 1, further comprising:
   detecting an R-wave by the sensing device via the housing-based electrodes;
   setting a P-wave sensing window in response to detecting the R-wave;
   verifying sensing of a P-wave preceding the detected R-wave by the sensing device by determining that the P-wave sensed by the sensing device was received during the P-wave sensing window; and
   enabling the generating of the trigger signal in response to verifying the sensing of the preceding P-wave.

3. The method of claim 2, wherein detecting the R-wave by the sensing device comprises:
   sensing the R-wave by the pacemaker;
   sending a wireless signal from the pacemaker to the sensing device in response to sensing the R-wave; and
   detecting the wireless signal by the sensing device.

4. The method of claim 2, further comprising automatically adjusting a P-wave sensing control parameter by the sensing device in response to not sensing the preceding P-wave during the P-wave window.

5. The method of claim 2, further comprising:
   determining, by the sensing device, a P-R interval between the preceding sensed P-wave and the detected R-wave;
   setting a pacing interval based at least in part on the P-R interval; and
   scheduling the trigger signal to be sent from the sensing device to the pacemaker at the expiration of the pacing interval.

6. The method of claim 5, further comprising:
   detecting a second R-wave during the pacing interval by the sensing device; and
   cancelling the trigger signal in response to detecting the second R-wave during the pacing interval.

7. The method of claim 6, wherein detecting the second R-wave comprises one of:
   sensing the second R-wave by the sensing device, and
   sensing the second R-wave by the pacemaker, transmitting an R-wave signal by the pacemaker to the sensing device in response to sensing the second R-wave, detecting the R-wave signal by the sensing device.

8. The method of claim 1, further comprising:
   scheduling the pacing pulse by setting a pacing interval by the pacemaker in response to detecting the trigger signal;
   sensing an R-wave by the pacemaker during the pacing interval; and
   cancelling the scheduled pacing pulse in response to the R-wave being sensed by the pacemaker during the pacing interval.

9. The method of claim 8, further comprising:
   sending a wireless ventricular event signal to the sensing device from the pacemaker in response to at least one of the R-wave sensed by the pacemaker during the pacing interval and the pacing pulse;
   detecting the ventricular event signal by the sensing device; and
   setting a P-wave blanking interval by the sensing device in response to detecting the ventricular event signal.

10. The method of claim 1, further comprising:
   sensing a preceding P-wave by the sensing device;
   setting an R-wave window by the sensing device;
   sensing an R-wave by the pacemaker;
   sending an R-wave signal from the pacemaker to the sensing device in response to sensing the R-wave;
   detecting the R-wave signal by the sensing device;
   enabling the trigger signal to be sent by the sensing device in response to the sensing device detecting the R-wave signal during the R-wave window.

11. The method of claim 10, further comprising:
   sending a P-wave signal from the sensing device to the pacemaker in response to sensing the preceding P-wave;
   determining a P-R interval by the pacemaker; and
   scheduling the ventricular pacing pulse by setting a pacing interval based at least in part on the P-R interval.

12. The method of claim 1, further comprising:
   sensing R-waves by the pacemaker;
   determining by the pacemaker an RR interval from one of a preceding R-wave sensed by the pacemaker and a preceding ventricular pacing pulse to the scheduled pacing pulse;
   comparing the RR interval to a minimum interval; and cancelling the scheduled pacing pulse in response to the RR interval being less than the minimum RR interval.

13. An implantable medical device system, comprising:
an extracardiac sensing device configured to be implanted outside the cardiovascular system, the extracardiac sensing device comprising:
a housing;
a plurality of housing-based electrodes;
a sensing module enclosed by the housing and configured to sense a P-wave attendant to an atrial activation of a patient's heart via the housing-based electrodes;
a trigger signal generator; and
a control module configured to control the trigger signal generator to transmit a trigger signal in response to the sensing module sensing the P-wave; and
an intracardiac pacemaker comprising;
a trigger signal detector;
a pacing pulse generator; and
a control module configured to schedule a pacing pulse in response to the trigger signal detector detecting the trigger signal.

14. The system of claim 13, wherein the sensing device control module is further configured to:
detect an R-wave attendant to a ventricular depolarization of the heart;
set a P-wave sensing window in response to detecting the R-wave;
verify sensing of a P-wave preceding the detected R-wave by determining that the P-wave sensed by the sensing device was received during the P-wave sensing window; and
enable the generating of the trigger signal in response to verifying the sensing of the preceding P-wave.

15. The system of claim 14, wherein:
the pacemaker further comprises:
a sensing module configured to sense the R-wave; and
a wireless signal generator configured to transmit a wireless signal in response to the sensing module sensing the R-wave; and
the extracardiac sensing device comprises a signal detector configured to detect the R-wave by detecting the wireless signal transmitted by the wireless signal generator.

16. The system of claim 14, wherein the sensing device control module is further configured to automatically adjust a P-wave sensing control parameter in response to not sensing the preceding P-wave during the P-wave window.

17. The system of claim 14, wherein the sensing device control module is further configured to:
determine a P-R interval between the preceding sensed P-wave and the detected R-wave;
set a pacing interval based at least in part on the P-R interval; and
schedule the trigger signal to be sent at the expiration of the pacing interval.

18. The system of claim 17, wherein the sensing device control module is further configured to:
detect a second R-wave during the pacing interval; and
cancel the trigger signal in response to detecting the second R-wave during the pacing interval.

19. An implantable, extracardiac sensing device, comprising:
a housing;
a plurality of housing-based electrodes;
a sensing module configured to sense cardiac electrical events via the housing-based electrodes, wherein the extracardiac sensing device is configured to be implanted outside a patient's cardiovascular system;
a trigger signal generator configured to transmit a wireless trigger signal to an intracardiac pacemaker to cause the pacemaker to deliver a cardiac pacing pulse;
a signal detector configured to detect a wireless event signal transmitted to the signal detector by the intracardiac pacemaker; and
a control module coupled to the sensing module, the trigger signal generator and the signal detector and configured to:
control the trigger signal generator to generate the wireless trigger signal in response to the sensing module sensing a cardiac electrical event;
set a blanking interval to inhibit sensing a next cardiac electrical event during the blanking interval in response to the signal detector detecting the wireless event signal transmitted by the intracardiac pacemaker.

* * * * *